(12) United States Patent
Vane et al.

(10) Patent No.: US 9,266,803 B2
(45) Date of Patent: Feb. 23, 2016

(54) LIQUID SEPARATION BY MEMBRANE ASSISTED VAPOR STRIPPING PROCESS

(75) Inventors: Leland M Vane, Cincinnati, OH (US); Franklin R. Alvarez, Cincinnati, OH (US)

(73) Assignee: The United States of America as represented by the Administrator of the U.S. Environmental Protection Agency, Washington, DC (US)

( * ) Notice: Subject to any disclaimer, the term of this patent is extended or adjusted under 35 U.S.C. 154(b) by 0 days.

(21) Appl. No.: 13/507,124

(22) Filed: Jun. 6, 2012

(65) Prior Publication Data

US 2013/0015052 A1    Jan. 17, 2013

Related U.S. Application Data

(63) Continuation of application No. 11/896,201, filed on Aug. 30, 2007, now abandoned.

(51) Int. Cl.

| | |
|---|---|
| C07C 29/80 | (2006.01) |
| B01D 1/28 | (2006.01) |
| B01D 3/00 | (2006.01) |
| B01D 3/14 | (2006.01) |
| B01D 3/38 | (2006.01) |
| B01D 61/36 | (2006.01) |
| C07C 29/76 | (2006.01) |
| C07C 45/78 | (2006.01) |

(52) U.S. Cl.
CPC . *C07C 29/80* (2013.01); *B01D 1/28* (2013.01); *B01D 3/002* (2013.01); *B01D 3/145* (2013.01); *B01D 3/38* (2013.01); *B01D 61/36* (2013.01); *C07C 29/76* (2013.01); *C07C 45/786* (2013.01); *B01D 2311/04* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,388,189 | A * | 6/1983 | Kawaguchi et al. | 210/490 |
| 4,444,571 | A * | 4/1984 | Matson | 95/48 |
| 4,906,256 | A * | 3/1990 | Baker et al. | 95/48 |
| 5,611,842 | A * | 3/1997 | Friesen et al. | 95/50 |
| 5,772,734 | A * | 6/1998 | Baker et al. | 95/42 |
| 6,059,857 | A * | 5/2000 | Ray et al. | 95/52 |
| 7,470,348 | B2 * | 12/2008 | Seiki et al. | 202/182 |
| 8,114,255 | B2 * | 2/2012 | Vane et al. | 203/12 |
| 8,263,815 | B2 * | 9/2012 | Huang et al. | 568/917 |
| 8,496,831 | B2 * | 7/2013 | Huang et al. | 210/640 |
| 2004/0222157 | A1 * | 11/2004 | Minhas et al. | 210/651 |
| 2008/0011680 | A1 * | 1/2008 | Partridge et al. | 210/640 |

FOREIGN PATENT DOCUMENTS

| | | | |
|---|---|---|---|
| EP | 0480567 A1 * | 4/1992 | |
| EP | 0485077 A1 * | 5/1992 | |

* cited by examiner

*Primary Examiner* — Christopher P Jones
*Assistant Examiner* — Adam W Bergfelder
(74) *Attorney, Agent, or Firm* — Hendricks and Associates

(57) ABSTRACT

An improved process for separation of liquid mixtures involves vapor stripping followed by mechanical compression of the vapor which is then exposed to a permeation membrane for separation of the compressed vapor. The apparatus for separating a liquid mixture of two or more solvents comprises components a stripping column, at least one overhead compressor and, thereafter, at least one selectively permeable membrane wherein the membrane separates the components of the vapor based on the different sorption and diffusion characteristics.

18 Claims, 22 Drawing Sheets

LIQUID SEPARATION BY MEMBRANE ASSISTED VAPOR STRIPPING PROCESS

This application is a continuation of U.S. application Ser. No. 11/896,201, filed Aug. 30, 2007, now abandoned.

FIELD AND BACKGROUND OF THE INVENTION

This invention relates to the field of separation of liquids using stripping means. The process of the invention involves vapor stripping followed by mechanical compression of the vapor which is then exposed to a permeation membrane for separation of the compressed vapor.

Distillation is the most common separation unit operation for miscible liquid mixtures in the chemical industry, including facilities producing ethanol. Although distillation has proven to be a robust and efficient method for removing and concentrating ethanol (EtOH) from fermentation broths, the energy efficiency of distillation declines dramatically below an ethanol concentration of 5 wt %. Processes proposed for the conversion of lignocellulosic biomass and waste materials to ethanol may deliver ethanol concentrations less than 5 wt %. As a result, processes which recover ethanol from water more efficiently than distillation at low concentrations will make lignocellulosic ethanol more economically viable. Further, standard distillation is only able to reach the ethanol-water azeotrope—about 5 wt % water. To reach fuel-grade water levels (<1.3 wt % water), distillation is typically followed by molecular sieve dryers. A process which could efficiently produce fuel grade ethanol from dilute ethanol would be of great interest. Such a process would also be useful for recovering ethanol from dilute process or waste streams not currently attractive due to the inefficiency of distillation, particularly in smaller installations in which the economies of scale do not favor distillation. Such a technology would also be useful for the separation of other organic solvents from water and separation of organic solvent mixtures.

Gas stripping, shown schematically in FIG. 1a (prior art), has been proposed as a method for recovering volatile products from fermentation broth. The ability of an inert gas to remove these products under mild temperature and pressure conditions is attractive. Unfortunately, the inert gas dilutes the volatile product, making recovery of the product by condensation more energy intensive. When the inert gas is replaced by only water vapor, as depicted in FIG. 1b (prior art), the process is called steam stripping. Although steam stripping is usually associated with high temperatures, operating the stripping column at reduced pressures enables operation at lower temperatures.

Both gas and steam stripping offer high degrees of separation when the vapor-liquid equilibrium (VLE) provides a strong concentrating effect or if the overhead condensate separates into two phases due to solubility limits of the components. However, in situations where the components are fully miscible and the VLE behavior is not highly favorable, stripping and overall separation efficiencies decrease. Such is the case for the separation of lower alcohols, such as ethanol, methanol, and propanol(s), from water. Due to the low partial pressure of the lower alcohols in a vapor phase in equilibrium with an alcohol-water solution (i.e. low activity), the volume of gas or steam required to strip a given mass of the alcohol is higher than for more volatile/less soluble compounds. In addition, lower alcohols are fully miscible with water in the overhead condensate. Finally, several of the lower alcohols form azeotropes with water, complicating the separation of the components in a VLE-based system.

Alternative technologies must be compared to the benchmark technology for the recovery of alcohols from water—distillation. According to Hawley's Condensed Chemical Dictionary ($14^{th}$ Ed.), "distillation" is defined as: "*A separation process in which a liquid is converted to vapor and the vapor then condensed to a liquid. The latter is referred to as the distillate, while the liquid material being vaporized is the charge or distilland. Distillation is thus a combination of evaporation, or vaporization, and condensation.*" Hawley's further defines "continuous distillation" as: "*Distillation in which a feed, usually of nearly constant composition, is supplied continuously to a fractionating column, and the product is continuously withdrawn at the top, the bottom, and sometimes at the intermediate points.*" According to Perry's Chemical Engineers' Handbook ($7^{th}$ Ed.) the fractionating column in distillation can be considered as being composed of two sections: "*If the feed is introduced at one point along the column shell, the column is divided into an upper section, which is often called the rectifying section, and a lower section, which is often referred to as the stripping section.*" The stripping vapor for the stripping section is generated in a reboiler which may be indirectly heated with steam or with a combusted fuel. Alternatively, a vapor, such as steam, may be directly introduced to the column to generate the stripping vapor.

The stripping section of the column acts to remove the more volatile compounds from the falling liquid so that the liquid exiting the bottom of the column (the "bottoms" stream) is depleted in those compounds which preferentially partition into the vapor phase. The rectifying section acts to deplete the rising vapor of the less volatile species, thereby enriching the rising vapor in the more volatile compounds. Thus, in distillation columns a portion of the rising vapor at the top of the column is condensed and returned to the column to cause rectification/enriching of the more volatile species. The returned condensate is called "reflux". At the bottom of the distillation column, a portion of the falling liquid is evaporated in the "reboiler" to create rising vapor. The reflux rate and the reboil rate are controlled to yield the desired operating conditions and compositions of the overhead and bottom product streams. The term "reflux ratio" is defined either as the ratio of liquid flow to vapor flow within the column (internal reflux ratio) or as the ratio of distillate returned to the column to the distillate withdrawn as product (external reflux ratio).

In conventional distillation columns, heat is added in the reboiler and removed in the overhead condenser. Although it acts to improve the separation performance of most distillation columns, return of reflux condensate to the column increases the heat required in the reboiler. In energy terms, the reboiler and overhead condenser are antagonistic. Thus, the reboiler heat required to perform a separation using a distillation column is greater than that required to simply strip the volatile species from the liquid.

The energy used to recover a unit mass of alcohol by distillation is a direct function of the feed concentration and reflux rate required to meet the desired product purity. As the concentration of alcohol decreases in the feed stream, the reflux rate increases and the amount of energy required to recover a unit mass of alcohol increases dramatically. This is shown graphically in FIG. 2 (Prior art) for the ethanol-water system as a gray area which represents a range of data provided in the literature for distillation processes. Also shown in FIG. 2 (prior art), as a horizontal line, is the heat of combustion of ethanol, about 30 MJ/kg. As indicated in the figure, the energy required to recover ethanol by distillation is low relative to the heat of combustion when the feed concentration is greater than 3 wt % ethanol. However, below 3 wt %, the energy of distillation rises rapidly and will exceed the heat of combustion when the feed concentration drops below 1 wt %. For this reason, the recovery of ethanol from streams containing less than 3 wt % is not very attractive from an energy standpoint.

In standard corn-to-ethanol production facilities, three separation columns (two stripping columns, one rectification column) combined with a molecular sieve dehydration system are used to recover ethanol from the fermentation broth and dry it to meet fuel specifications. Separate stripping and rectification columns are used instead of a single distillation column to improve heat integration, utilizing lower grade steam sources from within the recovery stage and from other unit operations in the facility. However, heat integration of this kind is more complicated to design/operate and requires additional equipment, thus increasing the capital cost. Such complexity is acceptable for larger scale operations, but becomes less so when the operation is scaled down and the relative cost increases. The beer still column, rectifier column, and side stripper column contain 22, 30, and 16 trays, respectively. Kwiatkowski et al. (J. R. Kwiatkowski, A. J. McAloon, F. Taylor, and D. B. Johnston, *Modeling the process and costs of fuel ethanol production by the corn dry-grind process*, Industrial Crops and Products, 23 (May 2006) 288-96) modeled the distillation system columns in a corn-to-ethanol facility with 34, 28, and 27 stages, respectively. Steam usage in those three columns treating 10.8 wt % ethanol broth totaled 25,146 kg/hr for an energy usage of 4.7 MJ/kg-ethanol (assuming 80% efficient boilers and an energy value of 2.26 MJ/kg-steam).

Prior art involving hybrid distillation-vapor permeation systems for alcohol-water separations rely upon rectification with condensed overhead vapor reflux liquid. The vapor feed to the vapor permeation system is either re-evaporated condensate or uncondensed overhead vapor. In all cases, however, a reflux condenser is an integral component of the system. Similarly, in hybrid distillation-pervaporation systems, the feed to the pervaporation system is condensed overhead vapor. Hybrid processes combining gas stripping with vapor permeation taught in prior art use non-condensable gases to remove volatile compounds from a liquid mixture. Other related prior art uses membranes to recover and recycle water vapor for the purpose of stripping non-condensable gases dissolved in liquids.

U.S. patent application Ser. No. 10/546,686 Ikeda (pub. no. US 2006/0070867 A1) "Method for concentrating water-soluble organic material". Ikeda '686 teaches a method for concentrating water-soluble organic material combining distillation with vapor permeation and includes heat recovery from either or both the permeated and non-permeated vapor either directly or indirectly in reboiler. Ikeda '686 teaches the use of a distillation column with complete condensation of the overhead vapor and a return of a portion of that condensed overhead as reflux to the rectification section of the column. No overhead compressor is taught therein.

U.S. Pat. No. 4,978,430 by Nakagawa et al. "Method for dehydration and concentration of aqueous solution containing organic compound". Nakagawa '430 teaches a combination of an "evaporation vessel", in which heat is provided but no reflux is involved, with a water-selective vapor permeation membrane system. The process of Nakagawa '430 relies upon the temperature of the evaporation vessel with an optional "adjusting valve" to set the feed pressure to the vapor permeation system. Thus, the membrane feed pressure for Nakagawa '430 is coupled to the evaporation temperature. No overhead compressor is included. The process of Nakagawa adds heat to the vapor prior to the membrane system and requires cooling to produce condensed permeate.

U.S. Pat. No. 5,273,572 Baker (1993) "Process for removing an organic compound from water". Baker '572 teaches the separation of organic compounds from water by gas stripping with organic compound removal from the gas using organic-selective membranes. Stripping gas may be recycled. Stripping gas may be water vapor i.e. "steam", but the steam is at least partially condensed before the stream, contacts the membrane unit. Overhead from stripper may be compressed. Stripper may operate at reduced pressure. However, the invention of Baker does not produce dry solvent.

U.S. Pat. No. 7,070,694 by Coiling et al., "Purification of fluid compounds utilizing a distillation-membrane separation process". Colling '694 teaches the combination of a distillation column, requiring reflux liquid for rectification with vapor permeation system for hydrocarbon purification. Coiling '694 teaches the use of a compressor on the vapor overhead from the column to raise the pressure of the vapor feed to the vapor permeation membrane and to enable recovery of latent heat from the overhead vapor by condensation of a portion of that overhead in the reboiler heat exchanger.

Sommer and Melin (2004) (S. Sommer and T. Melin, *Design and optimization of hybrid separation processes for the dehydration of 2-propanol and other organics*, Industrial & Engineering Chemistry Research, 43 (2004) 5248-59) discusses distillation-vapor permeation and distillation-pervaporation hybrids, all have reflux ("a pervaporation unit should be operated in such a way that the amount being separated by the membrane is as small as possible and withdrawn [from the distillation column] on the highest concentration level"). This article teaches against the presently disclosed invention.

Material published by Vaperma Inc. of St-Romuald, Quebec, Canada on their website www.vaperma.com shows a flow diagram of a process for producing ethanol in which overhead from a beer still is treated by membrane separation. No compression of the overhead stream from the still is shown, and the condensed permeate stream is returned to the fermentor, not the beer still. A presentation by Pierre Côté et al. at the International Fuel Ethanol Workshop in St. Louis, Mo. on Jun. 23, 2007, entitled *Field Demonstration of the Sifiek™ Membrane for Ethanol Dewatering*, and available subsequently on www.vaperma.com, shows a two-step membrane separation unit treating an ethanol/water mixture to create a dry ethanol product. The membrane separation steps operate under a driving force provided by a partial vacuum on the permeate side of the membranes.

U.S. Pat. No. 4,444,571 by Matson, "Energy-efficient process for the stripping of gases from liquids". Matson '571 teaches an energy-efficient process for the removal of a non-condensable or high vapor pressure gas (such as carbon dioxide or ammonia) from a liquid, such as water, which combines a stripping process with vapor permeation membrane system. The gas is separated from the vapor leaving the stripper by the membrane unit, enabling recovery of latent heat by return of the condensable vapor directly to the stripping column or by condensation in a reboiler heat exchanger. Matson '571 teaches the desorption of dissolved gases, either from water or organic solvents. It does not teach separation of water-organic solvent mixtures. In all of the claims in Matson '571, the membrane is "substantially permeable" to the condensable vapor while "substantially impermeable" to the noncondensable gas. The process of Matson '571 would not be appropriate for the separations to be performed with the present invention because both the permeate and retentate streams of the present invention contain condensable vapors while only one of the streams in Matson '571 is condensable. Matson '571 teaches that the gas-free permeate vapor is much more economically compressed from an energy standpoint than is the overhead from stripping column stating that "this method [compressing the entire overhead mixture] is impractical because of the large energy requirement associated with compressing the stripped gas present with the vapor". Thus, Matson '571 creates the membrane mass transfer driving force using a vacuum compressor only on the permeate stream which also enables recovery of the latent heat from the condensable permeate. In Matson '571, the membrane feed pressure is dictated by the temperature of the stripping column. The maximum pressure difference across the membrane is determined by the stripper pressure. Thus, the minimum membrane area according to the invention of Matson '571 can only be reduced by increasing the temperature of the stripper.

SUMMARY OF THE INVENTION

Figure 1:
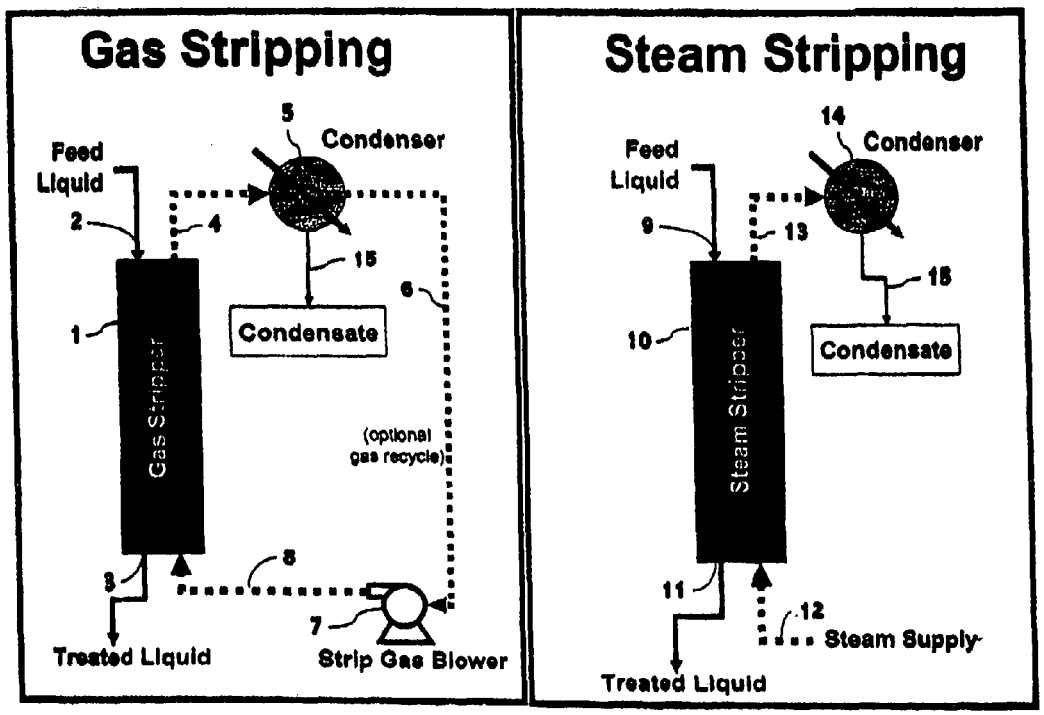
FIGS. 1(a) and (b) are schematic diagrams of the prior art gas (a) and steam (b) stripping apparatus for liquid treatment.

It is the object of this invention to provide means for separating mixtures of at least two liquid components in an energy efficient manner using apparatus especially adapted for such separations. The invention requires components through which streams of mixtures pass, a stripping column having at the top of said column, an inlet for a stream containing a feed liquid and an outlet for a stream containing vapor and, at the bottom of said column, an outlet for a stream of liquid that has passed through said stripping column and an inlet for a stream containing at least one vapor, said apparatus having further components located in relation to said stream exiting the top of said stripping column and arranged in sequence (1) at least one over-head compressor and, thereafter, (2) at least one selectively permeable membrane stage, arranged so that said stream exiting the said outlet at top of said stripping column passes through said compressor and contacts said membrane before exiting said apparatus. A preferred invention uses membrane stages which are selectively permeable to water.

DETAILED DESCRIPTION OF THE INVENTION

The present invention provides a process for separating liquid mixtures in an energy efficient manner. The process involves vapor stripping followed by mechanical compression of the produced vapor, followed by vapor permeation membrane separation of the compressed vapor, with recovery of latent and sensible heat from the vapor streams. The process is particularly suited for the production of fuel-grade ethanol from dilute fermentation broths. In the present invention, a simple vapor stripping column is used. The column does not have a condenser and, therefore, no rectifying section. No overhead condensate is returned to the top of the column to act as a reflux liquid. Thus, the amount of reboil energy required at the bottom of the column to strip out the more volatile compounds is a minimum. Instead of condensing the vapor overhead, the vapor from the stripper of the present invention is compressed and directed, as vapor, to the feed side of a permselective membrane. The membrane separates the components of the vapor based on the different sorption and diffusion characteristics of the components. The material which permeates through the membrane, termed the "permeate", will be enriched in one or more of the components of the feed vapor, while the material retained by the membrane, termed the "retentate", will be depleted in preferentially permeating species, while being enriched in the poorly permeating species. The permeate is also a vapor. Thus, no phase change occurs in the membrane separation process and, thus, no heat needs to be removed or added to accomplish a phase change in the membrane process.

In many instances, no outside heat source is required because the power provided to the compressor is sufficient to drive the process. The compressor facilitates recovery of latent and sensible heat, with the sum of heat recovered being several times greater than the power required by the compressor. According to the present invention, the ratio of heat recovered to compressor power added is at least about 3.0 and often greater than 4.0, making the process particularly energy efficient. Compressing the overhead vapor stream by at least about 100%, and more preferably by at least about 300%, prior to the membrane separation step achieves the significant energy savings.

The invention uses a combination of stripping, without rectification, and membrane separation. The mixture to be separated passes first through the stripping step, to create an overhead vapor that is enriched in the component of the mixture that more readily partitions into the stripping vapor. This component is usually the desired product of the process.

The overhead vapor stream is then compressed and separated in a membrane separation step. The compression step both provides a driving force for transmembrane permeation, by providing a feed stream at elevated pressure, and provides a reduced pressure in the column, which is exposed to the suction pressure of the compressor.

The membrane separation step produces a product stream further enriched in the desired component. The product stream may be either the residue or permeate stream from the membrane separation step, depending on the selectivity of the membrane. In general, processes in which the residue stream is the desired product are preferred.

The membrane separation step may itself be carried out in one or multiple steps, and product streams with high purity, such as greater than 99 wt % of the desired component, may be produced. The non-product stream from the membrane separation step is highly depleted in the desired component and highly enriched in the other component(s). Both the residue and permeate streams from the membrane separation unit are in the vapor phase. The non-product stream, usually the permeate stream, from the membrane separation step is returned to the stripping column, such as directly at the bottom of the column. The stream is returned in the vapor phase, thereby carrying back into the column all the sensible and latent heat associated with the stream. In this manner, much, most or all of the heat required to operate the column is provided by the return stream from the membrane.

The combination of membrane separation under pressure and recapture of heat energy from the streams leaving the membrane separation step provides a process that uses considerably less energy, in terms of megajoules per kilogram (MJ/kg) of desired product than distillation or any previous process. Instead of returning the vapor stream from the membrane separation step directly to the stripping column, the permeate or residue streams, or both, may be used to heat a reboiler for the column by heat exchange. This cools and partially or fully condenses these streams. The product stream is then withdrawn and the non-product stream is returned at an appropriate position in the column for further treatment. In either case, a stream containing the less-desired component is withdrawn as a bottoms liquid stream from the stripping column.

Transport of compounds through the membrane is dictated by the permeability of the membrane, mass transfer resistances in the feed and permeate sides of the membrane, as well as the fugacity driving force between the feed and permeate for each compound.

The rate of transport through the membrane is commonly termed the "flux". The flux J of component i through the membrane is represented as:

$$J_i = P_i(y_i^F P^F - y_i^P P^P) \quad \text{Equation 1}$$

where $P_i$ is the permeability of component i through the membrane, $y_i^F$ and $y_i^P$ are the mole fractions of i on the feed and permeate sides of the membrane, and $P^F$ and $P^P$ are the total feed and permeate pressures. In this equation, the resistance to mass transfer is assumed to be only that offered by the membrane and the fugacity driving force is replaced by the partial pressure driving force.

The present invention as exemplified herein results in recovery of fuel grade ethanol from water. This is not intended to imply the limitation of the invention to this specific solvent mixture. Other types of mixtures which the present invention can separate are described in the examples. In operation the overhead vapor from a vapor stripping column is in approximate equilibrium with the feed liquid. In this way, the overhead vapor from a vapor stripper being fed 5.0 wt % ethanol (balance water) would contain about 42 wt % ethanol while a feed of 1.0 wt % ethanol would yield a stripper overhead of 14 wt % ethanol. The purity of the overhead product from a distillation column is much higher because of the rectifying section of the column—approaching the ethanol-water azeotrope at 95.6 wt % ethanol, and is relatively independent of the feed concentration in the feed stream. Thus, the purity of overhead stream from a simple vapor stripping column is much lower than that of a distillation column and varies to a much larger degree on feed concentration than does the purity from a distillation column. The ASTM specifications for fuel-grade ethanol includes a 1 vol % (1.3 wt %) maximum for water. A purity target of >99.5 wt % ethanol (<0.5 wt % water) is common for processes producing fuel-grade ethanol. Thus, even the overhead condensate product from standard distillation requires purification to meet fuel specifications.

The energy required to evaporate the compounds which appear in the overhead vapor from a stripping column can be estimated from the heat of evaporation of the neat compounds (neglecting heats of solution/mixing). Normalized per unit of ethanol recovered, this heat of evaporation ($Q_{norm}^{evap}$) is estimated as follows:

$$Q_{norm}^{evap} \cong \frac{\sum_i H_i^{evap} N_i}{E_{EtOH}} \quad \text{Equation 2}$$

where $H_i^{evap}$ and $N_i$ are the heat of evaporation and overhead mass flow of species i, respectively. In the case of removing ethanol from water, the energy cost of delivering a unit of ethanol in the overhead product is the sum of the energy required to evaporate and condense both the desired ethanol and the undesired water in the overhead. In many systems, condensation occurs at an elevated temperature which allows for heat removal directly to the ambient environment with little energy input. Under such conditions, the main energy sink is the evaporation energy. When ethanol and water dominate the condensate, Equation 2 can be rewritten as:

$$Q_{norm}^{evap} = H_{EtOH}^{evap} + H_w^{evap}\left(\frac{C_w^V}{C_{EtOH}^V}\right) = H_{EtOH}^{evap} + H_w^{evap}\left(\frac{C_T - C_{EtOH}^L}{\alpha_{Ew} C_{EtOH}^L}\right) \quad \text{Equation 3}$$

where $C_i^V$ is the concentration of species i in the overhead vapor, $C_i^L$ is concentration of species i in the feed liquid, $C_T$ is the total concentration in the feed liquid, and $\alpha_{Ew}$ is the VLE separation factor for ethanol relative to water at the feed concentration. The separation factor for compound 1 relative to compound 2 is defined as:

$$\alpha_{12} = (C_1^V/C_2^V)/(C_1^L/C_2^L) \quad \text{Equation 4}$$

Figure 2:
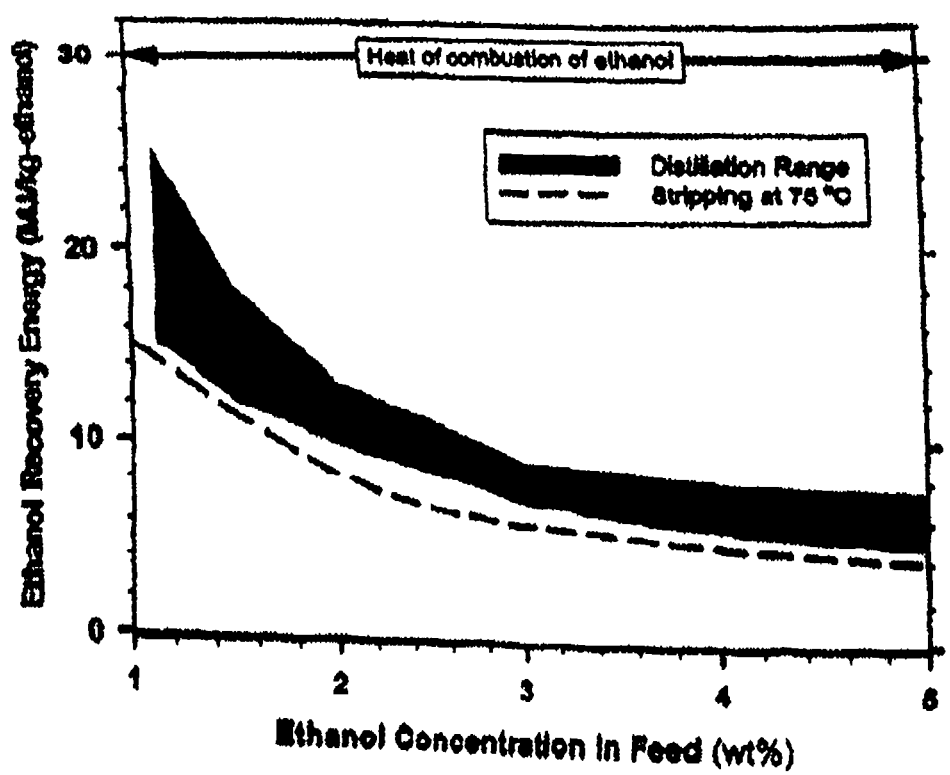
FIG. 2 is a graph showing energy requirements in recovery of ethanol from water by distillation.

On a molar basis, water and ethanol have similar heats of evaporation (40.7 vs. 38.6 kJ/mol). However, due to the difference in molecular weights, the heat of evaporation on a mass basis is significantly higher for water than for ethanol (2260 vs. 838 kJ/kg). Thus, if the condensate contains 50 wt % ethanol, 1 kg of water is evaporated per 1 kg of ethanol with 73% of the energy involved required for the water component. According to Equation 3, $Q_{norm}^{evap}$, is a minimum when $\alpha_{Ew}$ and $C_{EtOH}^L$ are maximized. Thus, as the concentration of ethanol in the feed stream decreases, the concomitant concentration of ethanol in the overhead vapor decreases, and the amount of water evaporated per unit ethanol increases. As a result, the amount of energy required to generate the overhead vapor per unit ethanol increases dramatically as the ethanol concentration decreases. Conversely, as the ethanol concentration increases, the energy required will asymptotically approach the heat of evaporation of ethanol (0.84 MJ/kg). The stripping energy calculated in this manner is shown in FIG. 2 as a dashed line. This line falls just below the literature distillation range, indicating that the energy required in distillation is mostly due to this stripping energy. The difference between the literature distillation energy usage values and the stripping energy usages is likely due to other energy sinks in the system (pumps, heat losses to atmosphere, heat exchange inefficiencies) which were not included in the simplistic stripping calculations according to Equation 2.

Comparing the Prior Art:

While some components of the present invention are disclosed in the prior art, the combination of process unit operations of the present invention has not been disclosed and would not have been obvious to one skilled in the art. The manner in which a stripping column is combined with a vapor permeation membrane system using vapor compression to achieve the energy efficient separation of miscible solvents, as exemplified by the production of dehydrated solvent and nearly solvent-free water from a solvent-water mixture, is not disclosed in prior art. In fact, the present invention is against established convention according to the literature and yields unanticipated energy efficiency because of the synergy of vapor compression for both heat recovery and membrane driving force and membrane separation to produce improved vapor streams which have improved energy and purity qualities.

Unlike in Ikeda '686, cited above, with the present invention, no overhead condenser is present and no reflux liquid is returned to the stripping column. In the present invention, steam is only required to provide auxiliary heat to the base of the stripping column (either directly or indirectly) and the driving force for membrane permeation is created by the compressor. The use of steam in Ikeda '686 to create the membrane feed vapor and to provide auxiliary reboiler heat makes the processes of Ikeda '686 significantly less efficient than the present invention. According to Embodiment 1 in Ikeda '686, 11,000 kcal/hr of steam is required to recover a 99.5 wt % ethanol product from a 10 wt % ethanol feed at a feed rate of 100 kg/hr (circa 9.9 kg/hr ethanol in product). This is equivalent to 4.65 MJ-steam/kg-ethanol which requires 5.8 MJ-fuel/kg-ethanol, assuming a standard boiler efficiency of 80%. Based on simulations of the present invention (as detailed in Example 2 of this application), production of 99.5 wt % ethanol from only 5 wt % ethanol would require a fuel energy of only 2.5 MJ-fuel/kg-ethanol assuming a fuel to electricity energy efficiency of 33% and electric motor efficiency of 75%.

Unlike the teachings of Matson '571, discussed above, in the method of the present invention, the membrane feed pressure and ability to recover sensible and latent heat is determined by the discharge pressure of the overhead compressor. Compression of the overhead vapor allows operation of the stripping column at reduced pressures (and therefore temperatures) while operating the membrane system at feed pressures which yield reduced membrane areas. The nature of the separation of Matson '571 is substantially different than that of the present invention. Matson '571 separates dissolved gases, such as carbon dioxide, from liquids such as water. In the present invention, the retentate stream from the membrane is a condensable compound and the use of an overhead vapor compressor allows for the recovery of the latent and sensible heat from the retentate stream in the stripper column.

From the above analysis, it is apparent that stripping columns have a small energy advantage over distillation columns for ethanol-water separation, that the main energy demand arises from the evaporation of water, and that the product purity from a vapor stripping column is low compared to that of a distillation column. In the present invention, the overhead vapor from a stripping column is compressed and fed to a vapor permeation unit. The latent and/or sensible heat of the non-permeating retentate stream and the permeate stream from the membrane system is recovered to provide most or all of the energy required to heat the vapor stripper. Variations of the present invention, termed Membrane-Assisted Vapor Stripping (MAVS) process, include use of water-selective membranes, as shown in FIG. 3 (a schematic flow diagram of the invention for the separation of ethanol from water using a vapor stripping column integrated with a 2-stage water-selective vapor permeation membrane system), or ethanol-selective membranes, as shown in FIG. 4 (a schematic flow diagram of the invention for the separation of ethanol from water using a vapor stripping column integrated with a single stage ethanol-selective vapor permeation membrane system).

Figure 3:
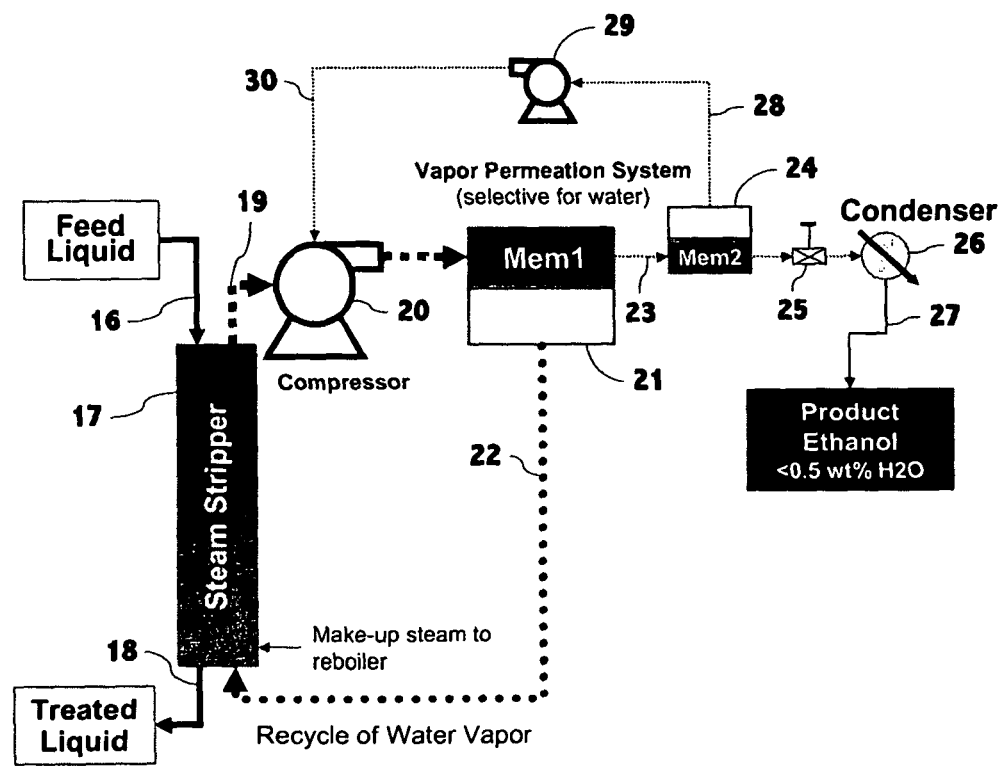
FIG. 3 is a schematic flow diagram of one embodiment using two compressors.
Figure 4:
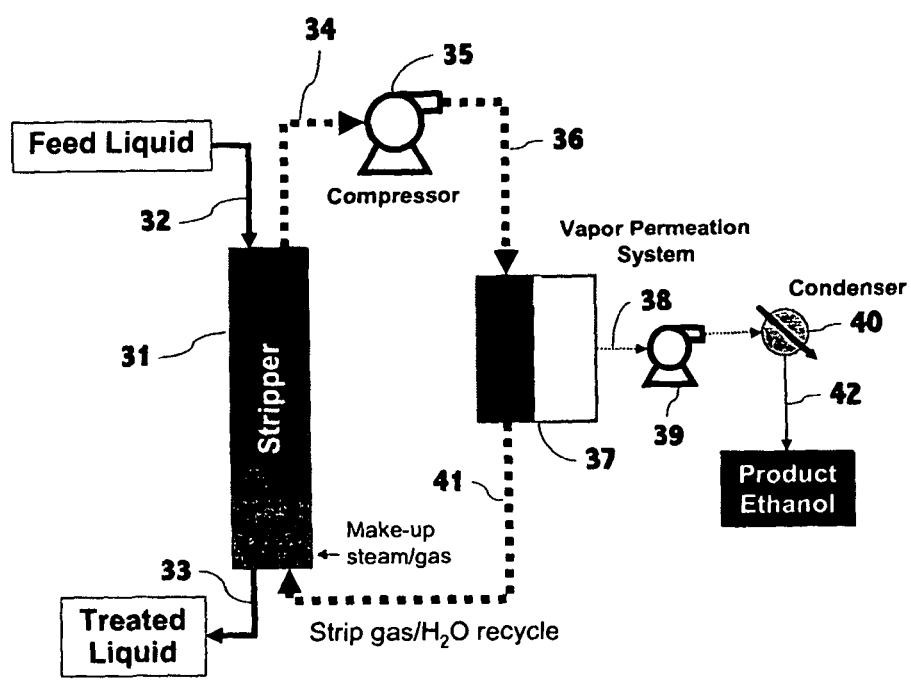
FIG. 4 is a schematic flow diagram using a single stage ethanol-selective vapor permeation membrane.

Although most examples provided in this application will focus on the general process of FIG. 3, many of the observations will be applicable to both options. In the case of ethanol-water separation, water-selective membranes are enlisted to dehydrate the ethanol and produce a water-rich permeate vapor. If the selectivity of the membrane is high enough, the permeate vapor may be returned directly to the base of the vapor stripping column to serve as the stripping vapor in the column. Otherwise, the vapor can be condensed in a reboiler heat exchanger, as seen in further drawings.

Figure 22:
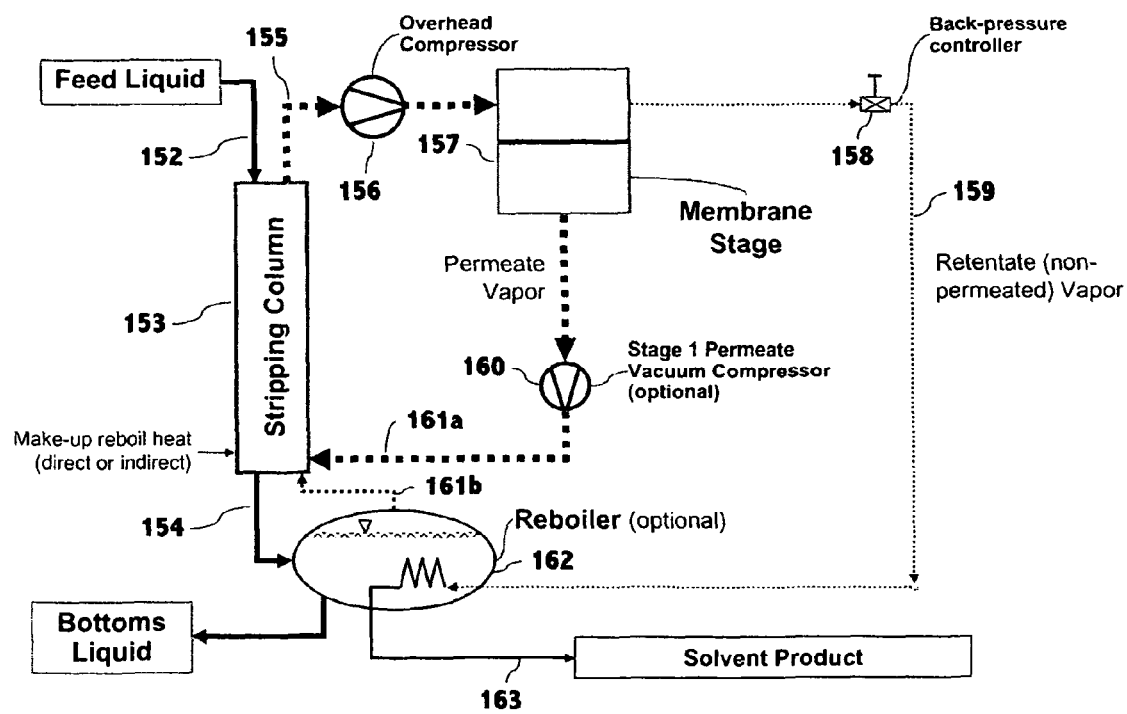
FIG. 22 is a schematic flow diagram of a single-stage membrane system in which the permeate from the membrane stage is returned as vapor to the stripping column.

As used herein, the terms "vacuum pump" and "vacuum compressor" both denote a device which increases the pressure of a gas/vapor stream wherein the pressure at the suction side of the device is below atmospheric pressure. The term "vapor compressor" denotes a device which increases the pressure of a gas/vapor stream wherein the pressure at the suction side of the device may be above, at, or below atmospheric pressure. The most basic configuration, that of a single-stage membrane system in which the permeate from that stage is returned as vapor to the base of the stripping column is shown in FIG. 22.

Referring with particularity to some of the preferred embodiments, in a first embodiment, the process of the invention includes the following steps:

(a) performing a stripping step comprising:

(i) introducing the liquid mixture as a feed stream to an upper region of a stripping column and allowing the feed stream to flow downwards in the column;

(ii) passing a rising vapor stream comprising solvent A up the column in mass- and heat-exchanging contact with the feed stream;

(iii) withdrawing from the stripping column a bottoms liquid stream enriched in solvent A relative to the feed stream;

(iv) withdrawing from the stripping column an overhead vapor stream depleted in solvent A relative to the feed stream;

(b) compressing the overhead vapor stream by at least about 100% using an overhead vapor compressor having an overhead suction side and an overhead discharge side, to form a compressed vapor stream at a first pressure;

(c) performing a membrane separation step, comprising:

(i) providing a first membrane having a first feed side and a first permeate side;

(ii) passing the compressed vapor stream across the first feed side;

(iii) maintaining a first permeate pressure on the first permeate side that is lower than the first pressure;

(iv) withdrawing from the first feed side a first retentate vapor stream depleted in solvent A relative to the compressed vapor stream;

(v) withdrawing from the first permeate side a first permeate vapor stream enriched in solvent A relative to the compressed vapor stream;

(d) returning at least a portion of the first permeate vapor stream to the column in such a manner that at least a part of the sensible and latent heat of the first permeate vapor stream is recovered as heat energy to drive the column.

In a second embodiment, the process of the invention includes the following steps:

(a) performing a stripping step comprising:

(i) introducing the liquid mixture as a feed stream to an upper region of a stripping column and allowing the feed stream to flow downwards in the column;

(ii) passing a rising vapor stream comprising solvent A up the column in mass- and heat-exchanging contact with the feed stream;

(iii) withdrawing from the stripping column a bottoms liquid stream enriched in solvent A relative to the feed stream;

(iv) withdrawing from the stripping column an overhead vapor stream depleted in solvent A relative to the feed stream;

(b) compressing the overhead vapor stream by at least about 100% using an overhead vapor compressor having an overhead suction side and an overhead discharge side, to form a compressed vapor stream at a first pressure;

(c) performing a membrane separation step, comprising:

(i) providing a first membrane having a first feed side and a first permeate side;

(ii) passing the compressed vapor stream across the first feed side;

(iii) maintaining a first permeate pressure on the first permeate side that is lower than the first pressure;

(iv) withdrawing from the first feed side a first retentate vapor stream enriched in solvent A relative to the compressed vapor stream;

(v) withdrawing from the first permeate side a first permeate vapor stream depleted in solvent A relative to the compressed vapor stream;

(d) returning at least a portion of the first retentate vapor stream to the column in such a manner that at least a part of the sensible and latent heat of the first permeate vapor stream is recovered as heat energy to drive the column.

In a third embodiment, the invention is an apparatus for carrying out the processes described above. The apparatus includes:

(a) a stripping column having an overhead vapor outlet, a stripping vapor inlet, a liquid mixture inlet and a bottoms liquid outlet, and adapted to permit rising flow of a stripping vapor and falling flow of the liquid mixture, the column having an internal pressure;

(b) a vapor compressor having a discharge side and a suction side, the suction side being in vapor-transferring connection with the overhead vapor outlet, the vapor compressor thereby determining the internal pressure;

(c) a first membrane separation unit containing a first separation membrane having a first feed side and a first permeate side, the first separation membrane being adapted to selectively permeate at least one component of the liquid mixture, the first feed side being in vapor-transferring connection with the discharge side, whereby the first feed side and the discharge side are at a substantially common pressure;

(d) a permeate-transferring line connected between the permeate side and the column, and adapted so that fluid may pass from the permeate side into the column.

Referring with particularity to the drawings, in FIG. 3 the feed liquid is delivered through the inlet area 16 into the stream stripper, 17, and the treated liquid having reduced ethanol passes through the outlet, 18. A stream containing the ethanol passes through outlet tube 19 to a compressor, 20 through an outlet, to contact a water selective permeable membrane 21. A stream of water-rich vapor 22 passes to the steam stripper for recycling through the stripper 17. The ethanol-rich retentate stream 23 that has not passed through the permselective membrane then is passed across a second selectively permeable membrane 24. The ethanol rich stream is then passed through a back pressure control, 25, through a condenser, 26, and out as a stream 27, as the final product. Additionally, the stream 28 from the permeate side of the membrane 24 may be looped through a second compressor 29 as stream 30 and then through compressor 20 for further recovery of ethanol.

Referring with particularity to FIG. 4, the vapor stripping column 31 is fed by an inlet stream of feed liquid 32, and has, at the bottom, an outlet 33 stream carrying liquid that has been treated in the stripper. The vapor stream 34 passes out through the top of the stripper and thence through a compressor 35. The stream 36 contacts an ethanol-selective permeable membrane 37. The retentate stream 41 containing water-rich vapor passes back into the stripper through an inlet on the bottom and the ethanol passes on through membrane 37 as stream 38 through compressor 39, thence through condenser 40 and out as stream 42, which is the desired product.

As shown in FIGS. 3 and 4 and mentioned above, MAVS systems require vapor compression prior to the membrane units. Additional vacuum pumps/compressors may be needed on the permeate streams of membrane units to deliver the desired transmembrane driving force (and reduce membrane area) or to raise the condensation temperature in downstream product condensers by increasing the partial pressure of the product to be condensed. A variety of system configurations covered by this invention are shown schematically in FIGS. 5 through 18, although the invention is not limited to these configurations.

Example 1

Effect of Non-Condensable Gas on Vapor Stripper, Compressor, and Membrane Systems As noted previously, the use of non-condensable gases to strip organic compounds from water followed by the recovery and reuse of the gas has been taught in prior art. In order to test whether the absence of non-condensable gases is advantageous according to the present invention, the efficiency and cost of the compressor and membrane systems required in the process for a hypothetical overhead vapor as a function of non-condensable gas content were estimated. The ethanol-water binary mixture was chosen as the model system. The chemical process simulation program ChemCAD 5.4 (ChemStations, Houston, Tex., USA) was used to perform steady state calculations. ChemCAD was also used for most equipment sizing and costing. Exceptions were liquid pumps, liquid storage tanks and distillation/stripping towers, for which literature sizing/costing relationships were used. Column height was based on an assumption of 1 ft (0.30 m) of height per VLE stage in the column. Column diameter was sized so as to avoid flooding in packed columns based on the Eckert correlation for an assumed pressure drop of 0.25" $H_2O$ per foot of packing (204 Pa/m or 1.5 torr/m). Natural gas and electricity were assumed to be the energy sources. In order to compare the energy usage of different technologies on the same basis, the fuel-equivalents for each energy source were determined. One MJ of electrical energy was assumed to correspond to 3 MJ of fuel-equivalents based on an assumed 33.3% fuel-to-delivered electricity efficiency. Similarly, 1 MJ of steam heat corresponded to 1.11 MJ of fuel-equivalents due to an assumed 90% boiler efficiency in this example. Membrane area calculations were performed based on a membrane with a 2 µm thick polymeric selective layer with a permeability of $1.54 \times 10^{-6}$ and $1.54 \times 10^{-9}$ $cm^3 \cdot cm/$ (cm²·s·cmHg) for water and ethanol, respectively, yielding a membrane with water and ethanol permeances of 7700 and 7.7 GPU, respectively, where 1 GPU=1×10⁻⁶ cm³(STP)/ (cm²·s·cmHg)=3.34×10⁻¹⁰ kmol/(m²·s·kPa). This assumed permeability was that observed for a poly(allyl amine-hydrochloride)-poly(vinyl alcohol) blend membrane developed in our laboratory. The ratio of the permeabilities, the permselectivity, is 1,000 in this example. The flux of component i through the membrane was calculated according to Equation 1.

The effect of stripping column pressure (which is also the suction pressure for the overhead compressor) and the discharge pressure of the overhead compressor (feed pressure to vapor permeation system) on compressor power, installed compressor cost, and membrane area was determined. These three items were identified as the cost components which vary significantly with column and compressor discharge pressure. Column cost will vary to a lesser extent because column diameter is relatively unaffected due to a relatively constant volumetric flow of vapor in the column for fixed ethanol production. A natural inclination would be to assume that reducing the stripping column pressure would increase capital and energy costs because the absolute suction pressure on the pump will be lower and the compression ratio required to deliver the same membrane feed pressure will be increased. In the case of steam stripping (i.e. with little or no non-condensable gases), this is generally a valid conclusion. However, in the case of gas stripping, operating the column at reduced pressures can result in lower compressor costs and lower membrane costs. This seemingly contradictory observation is discussed below. The size and power usage of the overhead vapor compressor(s) is determined primarily by the flow rate of vapor through the compressor (in moles of gas or gas volume at standard conditions), the suction pressure, and the discharge pressure. The first two of these variables determines the actual volumetric flow rate of vapor into the pump, often described in terms such as "actual cubic feet per minute" (ACFM). A first approximation of how much vapor must be processed to remove a given mass of alcohol from a solution in a gas stripping column is to calculate the partial pressure of the alcohol in equilibrium with the feed solution (assuming, to a first approximation, VLE between overhead vapor and feed liquid). Then, assuming ideal gas behavior, the moles of alcohol per unit volume of overhead vapor can be estimated. For example, if the aqueous feed liquid to a stripper contains 5 wt % ethanol at 35° C., the vapor in equilibrium with that solution contains ethanol at 12.8 torr and water at 41.25 torr. Thus, each m³ of overhead vapor contains 0.668 mol ethanol and 2.146 mol water. Therefore, in order to produce 1 million gallons of ethanol per year (MGY), i.e. 0.0948 kg/s, then 11,080 m³/hr of overhead vapor must be processed (assuming 100% ethanol recovery, 365 day 24/7 operation). This volume of vapor is independent of the total pressure of the overhead vapor. Thus, if a non-condensable stripping gas is present, then the total pressure will be above the combined partial pressures of ethanol and water (54 torr for the example here). In other words, the same actual volume of gas must be processed, independent of the pressure. With a non-condensable strip gas present, the compressor must process the same number of moles of ethanol and water as if the strip gas was not present, plus the moles of strip gas. If the total overhead pressure is 380 torr, then 54 torr is due to water+ethanol and 326 torr is due to the strip gas. Each m³ of overhead vapor still contains 0.668 mol ethanol and 2.146 mol water, but now it also contains 16.97 mol of the strip gas. The compressor still needs to process 11,080 m³/hr of overhead vapor to get 1 MGY ethanol, but now it must process 219 kmol/hr of total vapor compared to 31 kmol/hr if a column was operated with no strip gas and at 54 torr.

If the same compressor discharge pressure is desired, for example 2 atm-absolute (1520 torr), the compressor with suction at 54 torr has a compression ratio of 28 while the compressor with suction at 380 torr has a compression ratio of only 4. However, the actual volumetric flow rate into the suction side of the compressors is the same. In the end, the seven times higher molar flow rate for the 380 torr suction pressure case (gas stripping scenario) negates the advantage of having a compression ratio that is one-seventh that of the scenario without a stripping gas. In addition, the stripping gas has diluted the ethanol and water in the discharge vapor, reducing the driving force for any downstream membrane system, thereby increasing the required membrane area and possibly necessitating application of a lower absolute pressure on the permeate side of the vapor permeation membrane. In the case of the 380 torr suction gas stripping scenario, after a four-fold compression to 1520 torr, the partial pressures of ethanol and water are only four times higher—51 and 165 torr, respectively. On the other hand, for the column operating without a stripping gas (i.e. at 54 torr total pressure), the 28-fold compression to a discharge pressure of 1520 torr delivers a feed vapor to the vapor permeation module containing ethanol and water at partial pressures of 359 and 1155 torr, respectively. The partial pressure driving force is at least seven times greater without the strip gas, making the required membrane area one-seventh that estimated for systems utilizing a strip gas.

Figure 19:
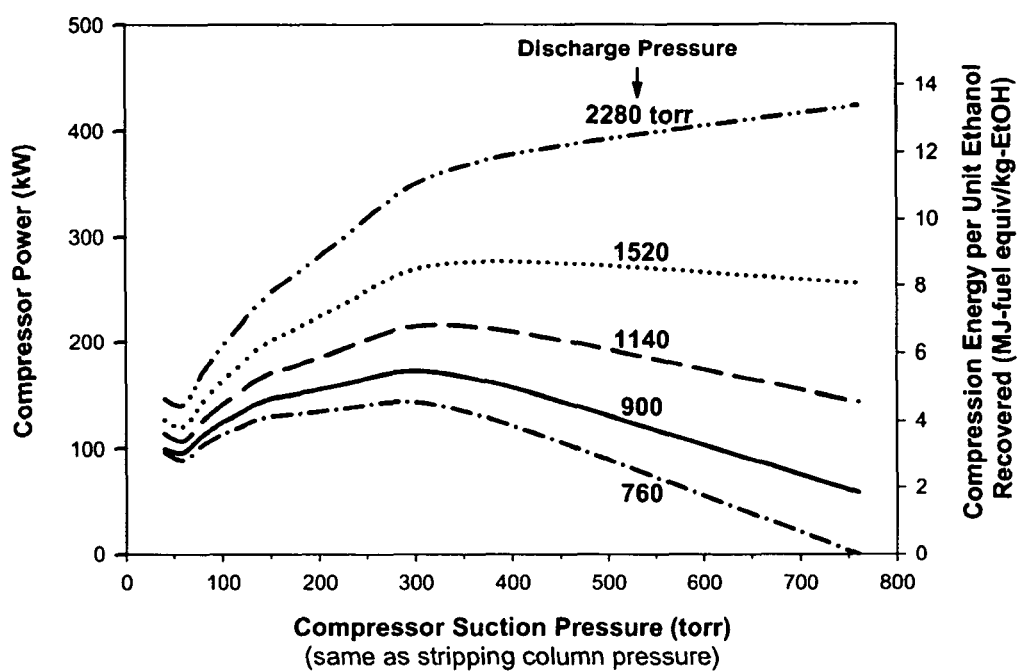
FIG. 19 shows effects of suction pressure and discharge pressure on the size of the overhead compressor.

Using ChemCAD, the size and installed cost of the overhead compressor as a function of column pressure and discharge pressure were determined for a stripping column treating a 5 wt % ethanol stream at 35° C. to produce 1 MGY of ethanol (equivalent to 7.4 kmol/hr or 341 kg/hr of ethanol). The compressor size, in terms of power and energy usage (in fuel equivalents) per unit ethanol is shown in FIG. 19 as a function of both the stripper column pressure (compressor suction pressure) and membrane feed pressure (compressor discharge pressure). The inert gas was assumed to be carbon dioxide.

Considering, with particularity, FIG. 19 shows effect of suction pressure and discharge pressure (membrane feed pressure) on the power usage of a hypothetical vapor compressor processing the overhead vapor from a gas stripping column. Compressor power usage and the resulting energy usage, in heat equivalents, per unit of ethanol product are shown as vertical axes. Stripping column is fed 5 wt % ethanol (balance water) and operates at a temperature of 35° C. at the top of the column. Feed contains sufficient ethanol to produce 1 million gallons per year of 100 wt % ethanol. An overall compressor efficiency of 90% was assumed for this level of analysis. The trends for capital cost of the compressor are similar to those for compressor power shown in FIG. 19 and are not displayed. The information presented in FIG. 19 demonstrates that operation of the gas stripper with a reduced pressure can result in reduced compressor size for a fixed discharge pressure. Comparing the compressor fuel-equivalents energy usage to the distillation energy usage range shown in FIG. 2, it is apparent that the compressor energy requirement is less than that required by distillation for many of the scenarios, particularly at low suction pressures.

Figure 20:
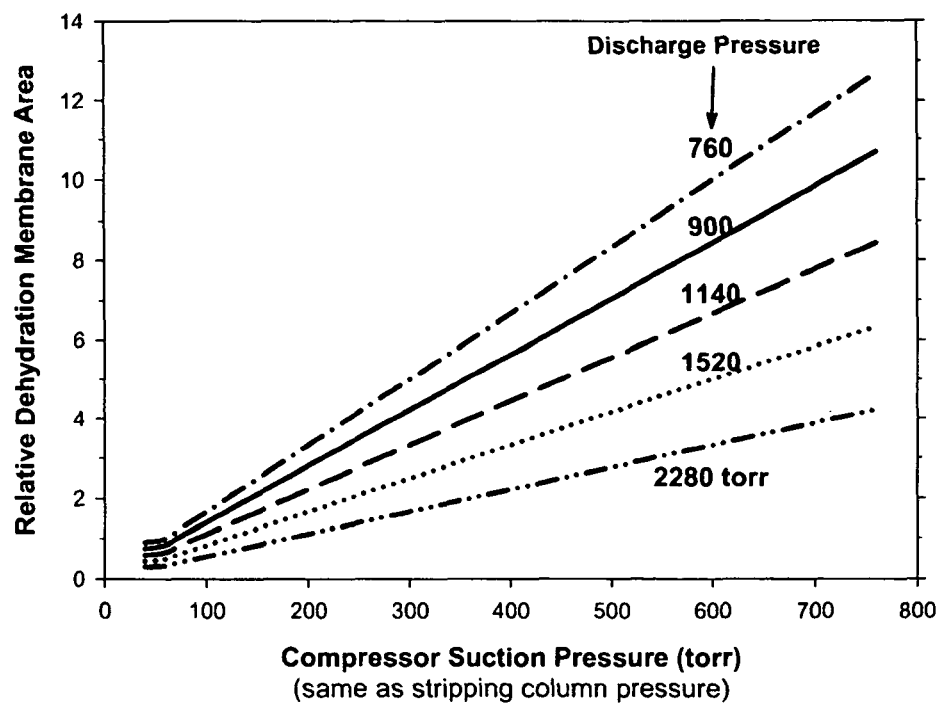
FIG. 20 shows the effect of suction pressure and discharge pressure on the relative amount of membrane area required to remove water from the overhead stream from a gas stripping column.

For the first level analysis, the amount of membrane area required to remove the water from the overhead strip vapor was estimated assuming a permeate pressure of absolute 0, assuming the area was proportional to the feed partial pressure of water, and normalizing by the "base case" membrane area required to remove water from the overhead for a stripping column operating at a total column pressure of 60 torr and a compressor discharge pressure of 760 torr. Membrane permeability was assumed to be the same for all scenarios. The normalized membrane area required to remove water is shown in the FIG. 20, which effectively shows the effect of suction pressure and discharge pressure on the relative amount of membrane area required to remove water from the overhead stream from a gas stripping column. Stripping column is fed 5 wt % ethanol (balance water) and operates at a temperature of 35° C. at the top of the column. Feed contains sufficient ethanol to produce 1 million gallons per year of 100 wt % ethanol. Areas have been normalized by the area calculated for 60 torr suction pressure and 760 torr discharge pressure. The values calculated suggest that the least membrane area will be required when the lowest suction pressure is applied and when the maximum discharge pressure is reached.

These estimates indicate that the least amount of non-condensable gas is desired. Thus, in the present invention, no non-condensable gas is intentionally added.

The equipment used and the layout of that equipment for use in the methods of the invention are as graphically depicted in the drawings and as disclosed in the examples. In each and every case, at a minimum, there is a vapor stripping column with an inlet for feed liquid at the top and an outlet for treated liquid at the bottom. There is also an outlet for vapor at the top of the stripping column. A stream of vapor from the stripper passes through a compressor and moves thence to contact with at least one permeation membrane and then is dispensed from the system. Additional passages interspersed with compressors and additional membranes may be present in the configuration. Furthermore, a permeate stream may be compressed further and may, additionally, be looped to pass through the stripper another time or be dispensed as the final product.

As vapors are compressed, heat is generated resulting in an increase in temperature. In order to protect the physical integrity of the compressor equipment or membrane equipment or for safety reasons, heat removal may be necessary within the compression step or between the compressor and the membrane system. This heat may be advantageously transferred to other streams within the process. For example, the heat of compression could be transferred to a reboiler heat exchanger to generate a portion of the stripping vapor in the column.

Referring to the figures: FIGS. 1(a) and (b) depict the prior art methods of gas and steam stripping wherein, in (a) 1 is the stripper, 2 is the inlet for the feed liquid, 3 is the outlet for the treated liquid, 4 the outlet leading to a condenser, 5 is the condenser, 6 is a stream to a strip gas blower, 7 is a gas blower and 8 is the stream back into the gas stripper. As to (b), 9 is the inlet into the stream stripper, 10 is the steam stripper, 11 is the outlet for treated liquid, 12 is the steam supply inlet, 13 is the outlet leading to the condenser, 14 is the condenser and 15 is the outlet from the condenser with the condensed product.

In theory, the MAVS system of the present invention reduces energy demand by recycling the water vapor which acts as the stripping phase. The energy usage per unit mass of recovered ethanol predicted by ChemCAD for a MAVS system of the present invention and two distillation systems described in the literature are shown in Table 2.1 and Table 2.2 for 1 wt % and 5 wt % ethanol in the feed liquid, respectively. Literature distillation values are used here without any efficiency conversions as if they were reported in fuel equivalents, although this was not stated in the papers. Thus, the literature values may underestimate the actual fuel equivalents required. Energy usage for the system of the present invention was well below that of the distillation systems despite the fact that the MAVS systems were producing a dry ethanol product (0.5 wt % water) while the ethanol product from the azeotrope-limited distillation systems was only 94 wt % ethanol and would require a separate dehydration step to meet fuel specifications. Energy usage for MAVS systems was found to be relatively independent of the water concentration in the ethanol product. Energy savings for the MAVS systems relative to the most efficient literature distillation technology (technology "C" from Madson and Lococo (2000) (P. W. Madson and D. B. Lococo, *Recovery of volatile products from dilute high-fouling process streams*, Applied Biochemistry and Biotechnology, 84-86 (2000) 1049-61)) for low-proof feed, thermally integrated stripper/rectifier) was 42 and 47% for feed streams containing 1 and 5 wt % ethanol, respectively. The energy required to produce fuel-grade ethanol with a MAVS system from 1 wt % ethanol (9.0 MJ-fuel equiv/kg-EtOH) was much lower than the fuel value of the ethanol product (30 MJ/kg), thus making it possible to produce ethanol with a positive net energy balance from even dilute streams.

TABLE 2.1

Energy required to produce concentrated ethanol from 1 wt % ethanol solution

| Separation Process | Product Purity (wt % EtOH) | Energy usage* (MJ/kg-EtOH) |
|---|---|---|
| Distillation, technology "C" from Madson and Lococo (2000). | 94 | 15.4 |
| Distillation from Galbe and Zacchi (2002) | 94 | 26.0 |
| Present Invention with 55° C. vapor stripping column (150 torr) and 760 torr overhead compressor discharge pressure | 99.5 | 9.0 |

*Energy usage in fuel equivalents for present invention, but the distillation scenarios are likely uncorrected for boiler efficiency
P. W. Madson and D. B. Lococo, Recovery of volatile products from dilute high-fouling process streams, Applied Biochemistry and Biotechnology, 84-86 (2000) 1049-61.
M. Galbe and G. Zacchi, A review of the production of ethanol from softwood, Applied Microbiology and Biotechnology, 59 (2002) 618-28.

TABLE 2.2

Energy required to produce concentrated ethanol from 5 wt % ethanol solution

| Separation Process | Product Purity (wt % EtOH) | Energy usage* (MJ/kg-EtOH) |
|---|---|---|
| Distillation, technology "C" from Madson and Lococo (2000) | 94 | 4.7 |
| Distillation from Galbe and Zacchi (2002) | 94 | 7.5 |
| Present Invention with 55° C. vapor stripping column (125 torr) and 760 torr overhead compressor discharge pressure | 99.5 | 2.5 |

*Energy usage in fuel equivalents for present invention, but the distillation scenarios are likely uncorrected for boiler efficiency Example 2

Production of Fuel-Grade Ethanol from Dilute Fermentation Broths

Figure 5:
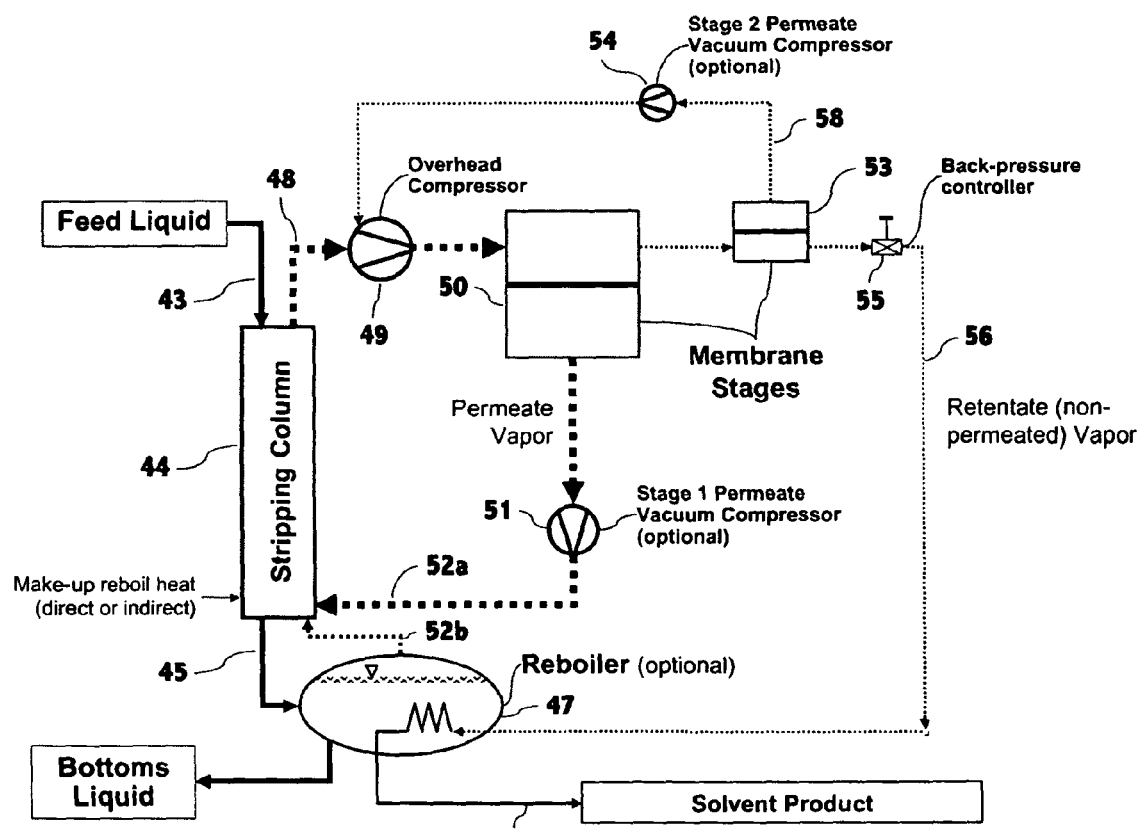
FIG. 5 is a schematic flow diagram wherein vapor passing through a selective membrane is returned to act as a stripping vapor

The energy usage and capital/operating costs according to the present invention were estimated for the recovery of ethanol from aqueous fermentation broths containing 1 or 5 wt % ethanol. The schematic diagram of the standard configuration of the present invention considered in this example is shown in FIG. 5, which is a schematic diagram of a process according to the present invention in which permeate from the first membrane stage is returned as vapor to act as stripping vapor in the stripping column. Permeate from second stage membrane is directed to the suction side of the overhead compressor. Retentate vapor is optionally condensed by heat exchange with the reboiler.

Referring with particularity to the drawings, in FIG. 5 there is the feed liquid stream, 43, which feeds into the stripping column, 44. A stream of bottoms liquid or treated liquid, 45, exits the bottom of the stripping column. Said bottoms liquid can be used as the source of liquid for an optional reboiler, 47. The desired solvent product is contained in the vapor stream, 48, which passes through a compressor, 49, and contacts selective membrane, 50. Vapor which has passed through the first permselective membrane stage, 50, is returned to the bottom of the stripping column as a vapor stream, 52*a*. Stream, 52*a*, containing permeate vapor, is compressed in a compressor, 51. The components from the column overhead vapor stream, 48, which do not permeate through the first selective membrane are then passed to a second membrane stage, 53, and the components which now pass through the selectively permeable membrane are returned as a vapor stream, 58, to the inlet of overhead compressor, 49, either directly or after being compressed in an optional compressor, 54. In this instance, the vapor which passes through the membrane 53 is now recycled as stream 58, and is recycled through compressor 49 and contacts membrane 50. A stream which is does not selectively pass through membrane 53 is retained (retentate or non-permeated vapor) and passes as stream 56. Stream 56 may have therein a back-pressure controller placed within the stream. The retentate containing the solvent product can then pass through a heat exchanger in thermal contact with the reboiler, 47, so that at least a portion of the product condenses. The condensing product causes liquid in the reboiler to vaporize, vapor created in this manner is returned to the stripping column as stream 52*b* and acts as a stripping agent. The final product is removed as stream 57.

The following relates to all of the FIGS. 5-18, 21, and 22:
1) Dashed lines indicate a vapor stream
2) Solid lines indicate a liquid stream
3) Heat exchange between feed liquid and bottoms liquid streams is optional and is not shown in the figures, although it may be advantageous
4) Interstage compressor heat removal/recovery and post-compressor heat recovery not shown, but may be necessary and/or advantageous
5) Although one, two or three membrane stages are shown in the figures, the system is operable with one or more stages
6) Recompression of retentate vapor between membrane stages is optional and may be advantageous to reduce membrane area or to increase the condensation temperature of the retentate
7) Heat from the various vapor streams may also be recovered by transfer to feed liquid.

Addressing FIGS. 6-18, in all instances the feed liquid is identified by the numeral 59, the stripping column is identified by the numeral 60, the rising gas/vapor streams are identified by the numeral 61 (when multiple vapor streams are fed to the column, they will be designated as 61*a* and 61*b*), the rising vapor stream exiting the top of the stripper is identified by the numeral 62 and a first compressor through which the rising vapor stream passes is identified by numeral 63. A first selectively permeable membrane is identified by the numeral 64 and the liquid stream exiting the bottom of the stripping column is identified as numeral 65. A back-pressure controller is identified by numeral 66. A second membrane stage is identified as numeral 67. The non-permeating retentate vapor stream exiting the last membrane stage is identified with numeral 68. A reboiler (which may be optional) is identified with numeral 69. A compressor, which may also be optional, on the permeate from the first membrane stage 64 is identified with numeral 70. The permeate vapor stream from the first membrane stage 64 is identified with numeral 71.

Figure 6:
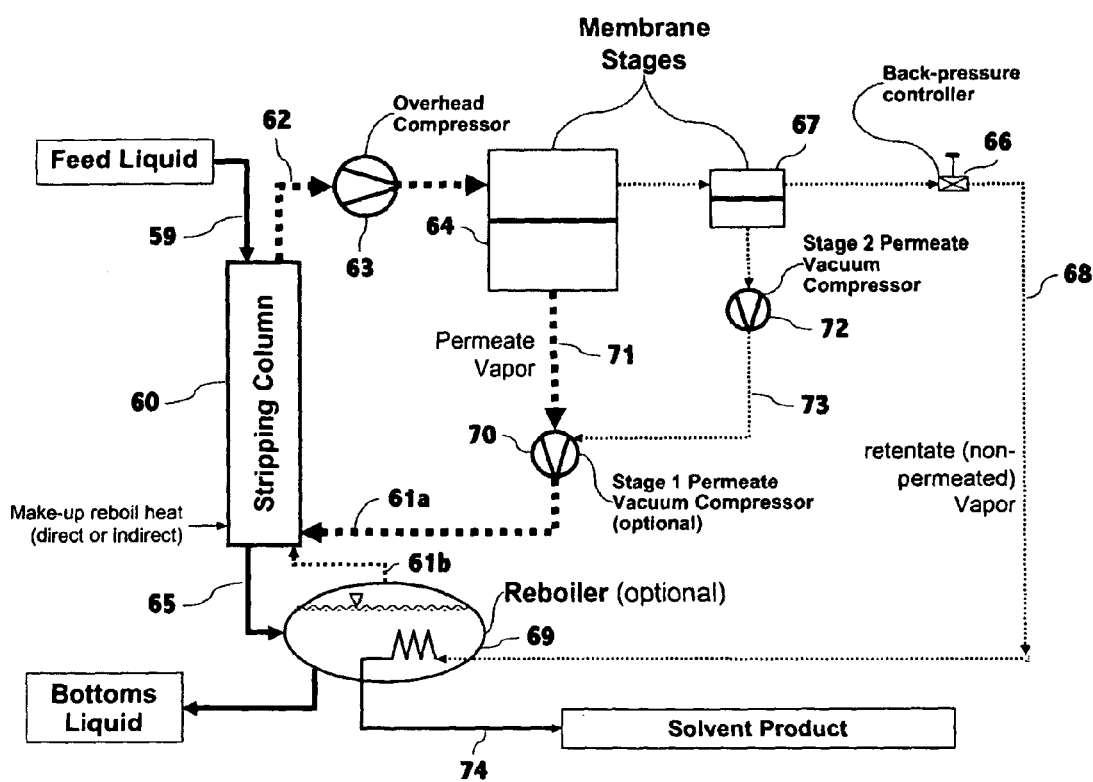
FIG. 6 is a schematic flow diagram showing the process wherein permeate from both first and second membrane stages are returned as vapor.

FIG. 6 is a schematic diagram of a process according to the present invention in which permeates from both the first and second membrane stages are returned as vapor to act as stripping vapor in the stripping column. The membranes both selectively allow water to pass through to be returned to the column as steam. Retentate vapor is (optionally) condensed by heat exchange in the reboiler, 69. All or a portion of bottoms liquid stream 65 may be directed to the optional reboiler 69. The vapor stream exiting the top of the stripping column will pass through the overhead compressor, 63, and then contact a water-selective permeable membrane, 64. The permeate vapor stream 71 passes back to the stripping column as incoming stripping stream 61*a*.

Optional compressor 70 can be used to compress the permeate vapors before returning to the stripping column. The retentate from membrane 64 is then contacted with a second membrane, 67, for further selective removal of water vapor. Permeate vapor from water-selective membrane 67 is compressed in compressor 72 and passes on as stream 73 to mix with stream 71 and then is further compressed in compressor 70, if present. The vapor stream, 68, containing the retentate from the membrane stages then passes through a back-pressure controller, 66, as the solvent product. The retentate vapor containing the solvent product, 68, can then pass through a heat exchanger in thermal contact with the reboiler, 69, so that at least a portion of the product condenses. The condensing product causes liquid in the reboiler to vaporize, vapor created in this manner is returned to the stripping column as stream 61*b* and acts as a stripping agent. The final product is removed as stream 74. It is not necessary, in order to practice the invention, to have either a reboiler or a back pressure controller. However, the use of the reboiler may effectively recapture energy in a system. The back pressure may further increase efficiency of the system.

Figure 7:
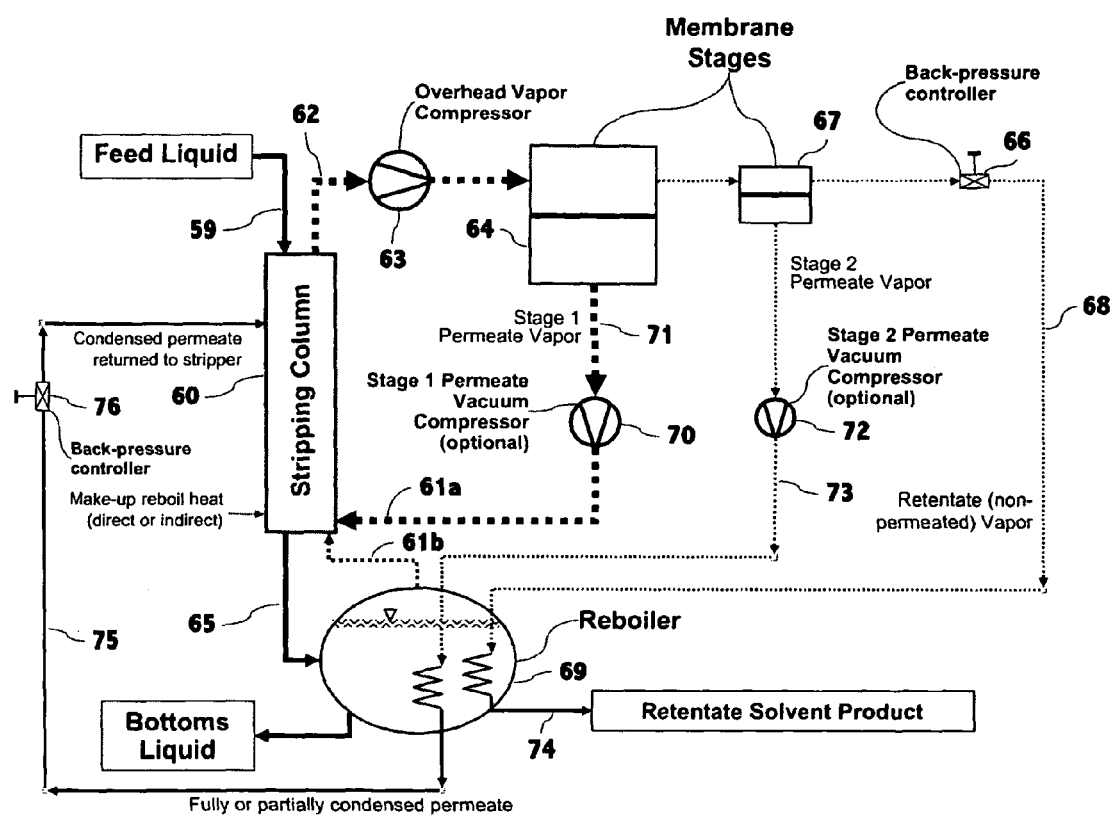
FIG. 7 is a schematic flow diagram wherein a reboiler is used to condense permeate which passes through a second membrane.

The apparatus of FIG. 7 differs from that of FIG. 6 only in that the vapor permeate stream, 73, from the second membrane stage, which may be subject to compression in compressor 72 is not passed through compressor 70, but is passed through a heat exchanger in thermal contact with the reboiler, 69, so that at least a portion of the vapor in stream 73 condenses. The condensing vapor causes liquid in the reboiler to vaporize, reboiled vapor created in this manner is returned to the stripping column as part of stream 61*b* and acts as a stripping agent. The partially or fully condensed permeate vapor from the second membrane stage is returned to the stripping column, 61, as stream 75 through back-pressure controller 76. As in FIG. 6, the retentate vapor, 68, may, optionally, pass through a heat exchanger in thermal contact with reboiler 69. The vapor permeate 71 from the first membrane stage 64 is returned, as vapor, to the stripping column as stream 61*a*. Compressor 70 may be used to increase the pressure of permeate 71 prior to returning to the stripping column as stream 61*a*.

Stripper temperature and compressor discharge pressure can be varied. In FIG. 5, two water-selective membrane stages are operated in series to dehydrate the compressed overhead. The permeate from the first membrane stage is directly returned to the bottom of the stripping column and is comparable to superheated steam. Thus, the permeate pressure of the first membrane stage is the same as the column pressure. In this way, energy is conserved by returning the stripping material—steam—to the column without a condensation or evaporation step. The compressor provides the driving force for transport across the membrane and the membrane provides the selectivity required to return the water vapor directly to the bottom of the column. A second membrane stage is needed to reduce water concentration down to the target of 0.5 wt % in the product ethanol. Due to partial pressure driving force limitations as the water mole fraction in the ethanol vapor stream decreases, the permeate pressure in the second membrane stage may need to be reduced relative to that of the first stage. Thus, a second compressor/vacuum pump operating on the permeate from the second membrane stage is shown as an option in FIG. 5. When present, this compressor raises the pressure of the second membrane stage permeate to match the suction pressure of the overhead compressor.

The main cost and energy consuming components include the overhead compressor, second stage membrane permeate vacuum pump, stripping tower, process heat exchangers, and the membrane units. In all, 19 capital cost components were considered in the analysis. The basis assumptions for the simulations were as follows:
1) Plant size: 1 MGY ethanol product (0.0948 kg/s)
2) Feed: 1 or 5 wt % EtOH
3) Product: 99.5 wt % ethanol
4) Bottoms from stripper column: 0.02 wt % ethanol
5) Stripping column operates with no inert strip gas present
6) Stripper has 18 stages which are 100% efficient, total height=5.5 m
7) Vapor permeation water-selective membrane with water permeance of $7.7 \times 10^3$ $cm^3(STP)/cm^2 \cdot s \cdot cmHg$ ($2.6 \times 10^{-6}$ $kmol/m^2 \cdot s \cdot kPa$) and a water-ethanol permselectivity=1000.
8) Overall compressor and pump efficiency: 75%
9) All equipment 316 stainless steel (SS) except compressors (carbon steel) and feed tank.
10) Permeate vapor from membrane stage 1 directly returned to bottom of stripper.

Figure 11:
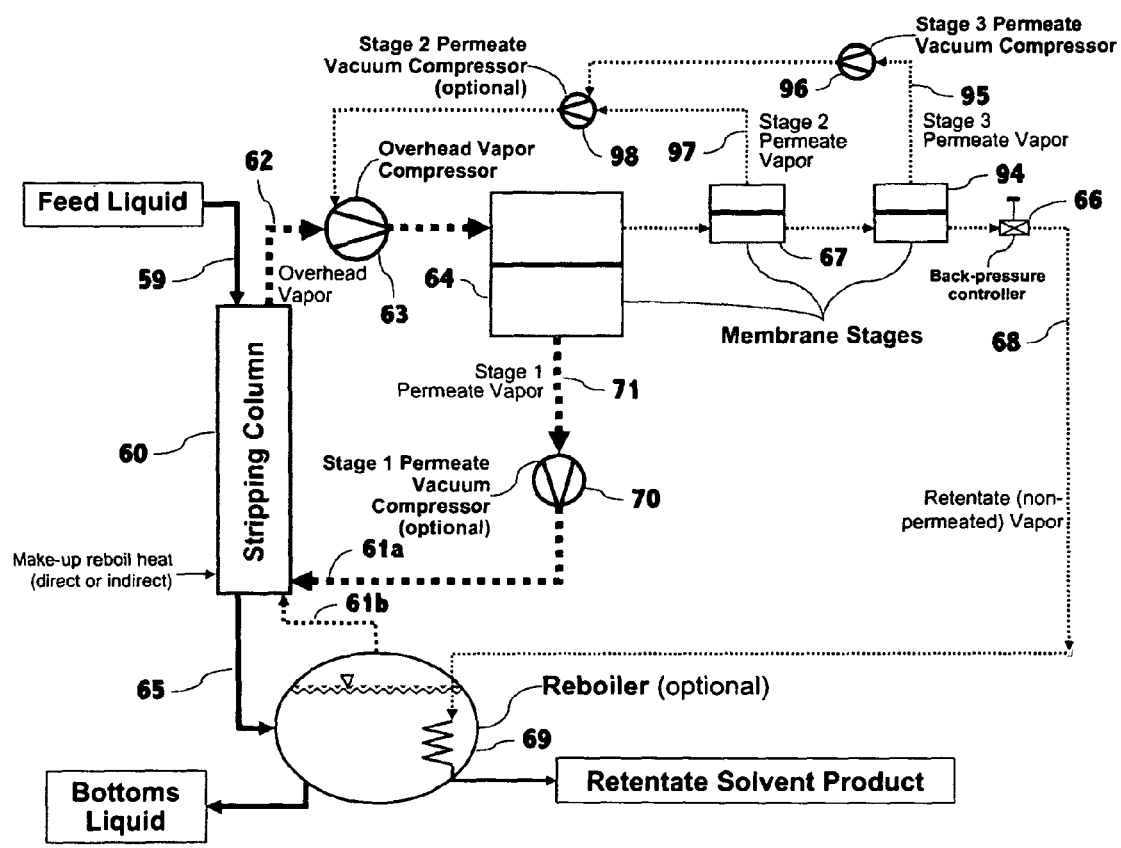

Membrane area was determined using a MICROSOFT EXCEL™ spreadsheet in which the membrane system was divided into membrane subunits each removing circa 10% of the water in the feed to that individual subunit. Through an iterative process, the average feed and permeate pressures in each subunit were estimated as was the membrane area. When the water partial pressure difference between the feed and permeate in a downstream membrane subunit dropped to a fraction (usually 5 or 10%) of that in the first membrane subunit, the permeate pressure was reduced by a factor of 3 or more for all subsequent subunits indicating the need for a vacuum compressor for that stage of membrane, otherwise mass transfer would effectively cease. As is common in vapor permeation calculations, feed pressure was assumed to be constant, although the composition was allowed to change as water was removed. The composition and flow rate of permeate from a particular membrane stage was determined by compositing the permeate streams from the subunits in that stage. The permeate streams from membrane stages 1 and 2 were entered into the ChemCAD simulator as feed streams to the bottom of the stripper (after passing through a heat exchanger) and to the vacuum pump for the second membrane stage, respectively. In a few scenarios, a third membrane stage with a lower permeate pressure than the second membrane stage (along with a separate compressor/vacuum pump for the third stage) was required to achieve the target 0.5 wt % water in the ethanol retentate. The schematic diagram for the three-stage scenario is shown in FIG. 11, which is a schematic diagram of a process according to the present invention consisting of three membrane stages in which permeate from the first membrane stage is returned as vapor to act as stripping vapor in the stripping column. Permeate from second and third membrane stages is returned to the suction side of the overhead compressor. Retentate vapor is optionally condensed by heat exchange with the reboiler. The streams may be carried in tubing of almost any material so long as the contents of the stream passing through the tubing does not interact with the material from which the tubing is made. In an industrial process, the tubing would most likely be made of some metal that is inert in the presence of the streams flowing through the system.

Example 3

Effect of Stripper Pressure and Compressor Discharge Pressure on Energy Usage

In example 2, the calculated energy benefits of the present invention relative to that of distillation were presented for the separation of ethanol/water mixtures. In that example, the operating temperature of the stripping column for the present invention was fixed at 55° C. In this example, the effect of stripper temperature (which determines the stripper pressure) and of the overhead compressor discharge pressure (which is the same as membrane feed pressure in the present invention) on energy usage for the present invention are calculated for ethanol-water mixtures of 1 and 5 wt % ethanol. The general basis assumptions are the same as those in Example 2 and generic schematic diagrams for the 2- and 3-membrane systems for this example are the same as those in Example 2 and are presented in FIGS. 5 and 11. Raising stripper operating temperature also raises the operating pressure of the stripper, thereby increasing the suction pressure of the overhead compressor. For a fixed compressor discharge pressure, increasing the stripper operating temperature thus reduces the size and energy usage of the overhead compressor. The permeate vapor from stage 1 of the membrane system is assumed to be returned directly to the bottom of the stripping column. As a result, increasing stripper temperature also results in a higher permeate pressure which leads to higher membrane areas.

The results of the computer process simulations according to the present invention are presented in Tables 3.1 and 3.2 for 1 wt % and 5 wt % ethanol in the feed liquid, respectively. From this information and that presented in Example 2, it is evident that the present invention can be used at a wide range of temperatures and still require less energy than standard distillation systems. Further, it is evident that increasing stripper temperature from 35 to 65 degrees should reduce energy usage by about 50%. For the same temperature increase, the required membrane area is estimated to increase 66%. This increase in membrane area can be counteracted by increasing the discharge pressure of the overhead compressor. Thus, the economic tradeoff between energy usage, compressor size, and membrane cost would have to be considered.

TABLE 3.1

Effect of Stripper Temperature and Overhead Compressor Discharge Pressure on the Energy required to produce 99.5 wt % ethanol from a 1 wt % ethanol feed solution.

| Stripper Temperature[#] (° C.) | Stripper Pressure (torr) | Overhead Compressor Discharge Pressure (torr) | Energy usage* (MJ/kg-EtOH) |
|---|---|---|---|
| 35 | 45 | 760 | 13.8 |
| 45 | 76 | 760 | 11.3 |

TABLE 3.1-continued

Effect of Stripper Temperature and Overhead Compressor Discharge Pressure on the Energy required to produce 99.5 wt % ethanol from a 1 wt % ethanol feed solution.

| Stripper Temperature[#] (° C.) | Stripper Pressure (torr) | Overhead Compressor Discharge Pressure (torr) | Energy usage[*] (MJ/kg-EtOH) |
|---|---|---|---|
| 55 | 125 | 760 | 9.0 |
|  |  | 900 | 9.9 |
|  |  | 1140 | 11.3 |
| 65 | 198 | 760 | 7.1 |
|  |  | 1140 | 8.8 |
| 98.6 | 760 | 2280 | 9.2 |

[#]Temperature at top of column
[*]Energy usage in fuel equivalents

TABLE 3.2

Effect of Stripper Temperature and Overhead Compressor Discharge Pressure on the Energy required to produce 99.5 wt % ethanol from a 5 wt % ethanol feed solution.

| Stripper Temperature (° C.) | Stripper Pressure (torr) | Overhead Compressor Discharge Pressure (torr) | Energy usage[*] (MJ/kg-EtOH) |
|---|---|---|---|
| 55 | 150 | 760 | 2.50 |
|  |  | 1140 | 2.94 |
| 94.1 | 760 | 2280 | 3.34 |

[*]Energy usage in fuel equivalents

Example 4

Figure 8:
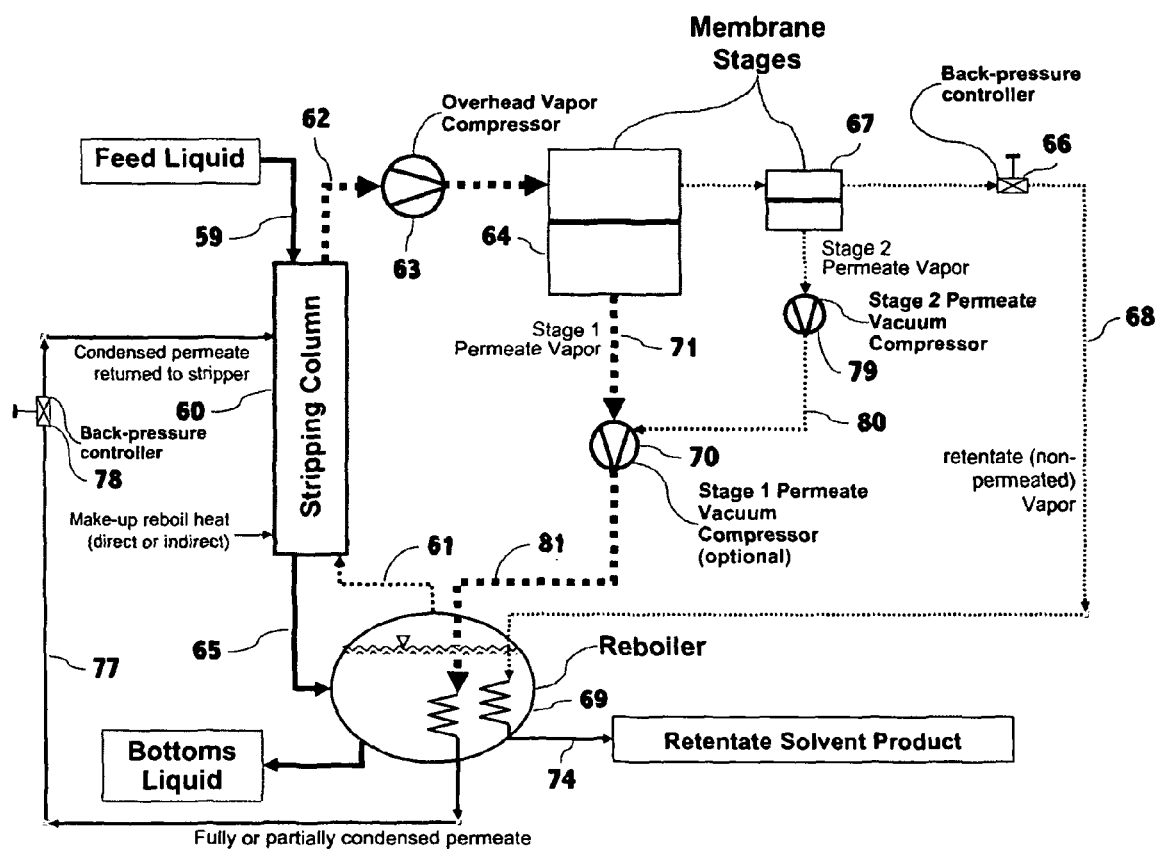
FIG. 8 is a schematic drawing wherein the non-permeating vapor is condensed in the reboiler.

Production of High Purity Ethanol from 11.5% Ethanol Feed Using Less Selective Membranes In Examples 2 and 3, highly water-selective membranes (water/ethanol permselectivity of 1,000) were assumed in calculations. This allowed the permeate vapor from the first membrane stage to be directly returned to the column as vapor. In some situations, however, membrane selectivity may be lower, making it impossible to return the permeate vapor directly to the column due to target discharge concentrations of ethanol in the bottoms stream from the stripper column. In this example, a water/ethanol permselectivity of only 100 is assumed. In this case, the latent and sensible heat of the permeate vapor is recovered by condensing the permeate vapor in a reboiler heat exchanger using a vacuum compressor to increase the pressure of the permeate vapor. The schematic diagram for the process is shown in FIG. 8 which is a schematic diagram of a process according to the present invention in which permeate from both the first and second membrane stages is condensed in a reboiler heat exchanger. Retentate vapor is condensed by heat exchange with the reboiler. The basic assumptions for the simulations were as follows:
1) Plant size: 50 MGY ethanol product
2) Feed: 11.5 wt % EtOH
3) Product: 99.7 wt % ethanol
4) Bottoms from stripper column: 0.02 wt % ethanol
5) Stripping column operate wirh no inert strip gas present
6) Stripper has 24 stages which are 100% efficient
7) Vapor permeation water-selective membrane with water permeance of $2.0 \times 10^{-3}$ cm$^3$(STP)/cm$^2$·s·cmHg ($0.67 \times 10^{-6}$ kmol/m$^2$·s·kPa) and a water-ethanol permselectivity=100.
8) Overall compressor and pump efficiency: 75%
9) All equipment 316 stainless steel (SS) except compressors (carbon steel) and feed tank.
10) System pressures:
 a. Stripper=380 torr
 b. Overhead compressor discharge=1500 torr (295% compression)
 c. Membrane Stage 1 Permeate=380 torr
 d. Membrane Stage 2 Permeate=25 torr
 e. Membrane Stage 1 vacuum compressor discharge=900 torr
 f. Membrane Stage 2 vacuum compressor discharge=380 torr The ChemCAD process simulations for this example predict an energy usage of 2.30 MJ-fuel equiv/kg-EtOH. Thus, despite the need for additional compressor capacity relative to the processes described in Examples 2 and 3, the energy usage in this example is still quite small. The three compressors in this example use a total of 3474 kW in power (1797, 994, and 683 kW for the overhead, Stage 1 permeate, and Stage 2 permeate compressors, respectively) while a total of 15,523 kW of energy is recovered in the reboiler from within the process. Of that recovered energy, 63% is from condensed permeate, 30% from condensed retentate product, and 7% from heat removal from the overhead compressor. Only 411 kW of auxiliary reboiler energy is required with 89% of energy added to the system going to power the compressors. The ratio of energy recovered within the process to the energy required for the compressors is 4.5.

Referring with particularity to FIG. 8, the second stage membrane 67 is shown. A reboiler, 69, is a means of recapturing energy from the retentate stream 68 as it passes to collection. The permeate stream, 80, from the second membrane, 67, is compressed in compressor 79 and joins the permeate vapor stream, 71, from the first membrane, 64. The combined permeate streams, 81, may be compressed in compressor, 70, if present. The combined permeate vapor streams, 81, are at least partially condensed in a heat exchanger in thermal contact with reboiler, 69, before returning to stripping column 61 as stream 77 through back-pressure regulator 78.

Figure 9:
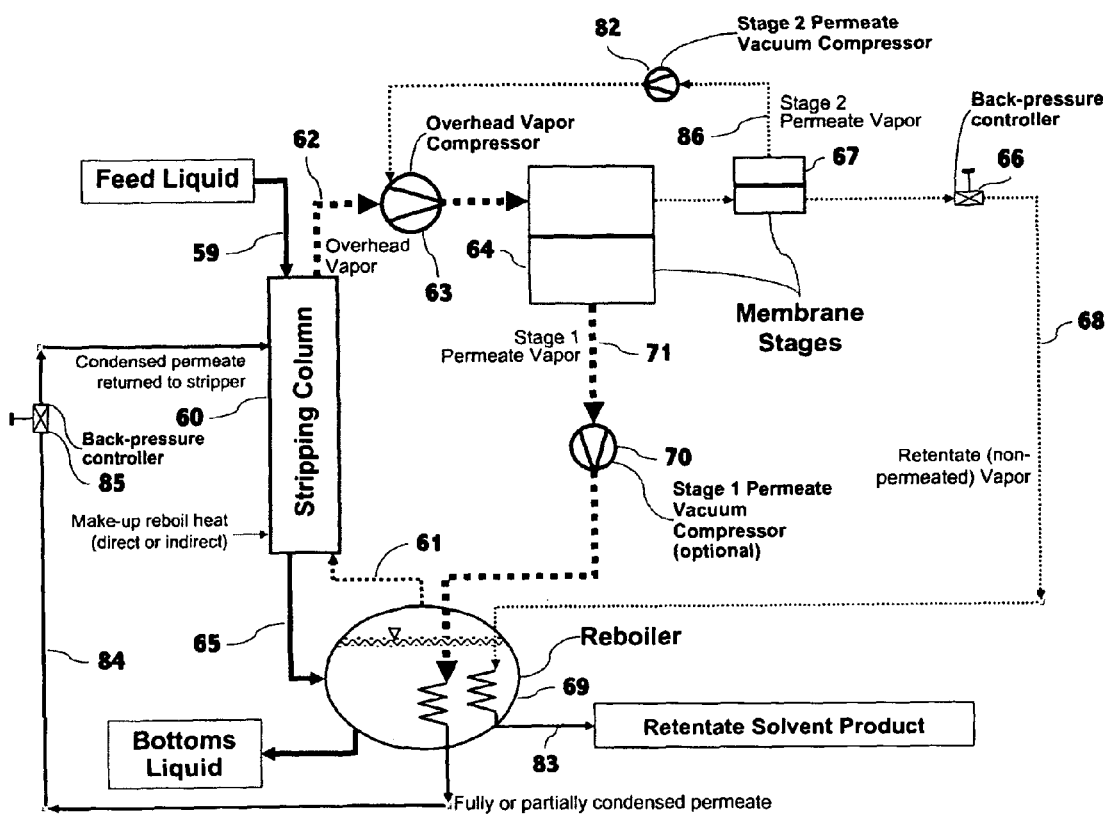
FIGS. 9 to 18 are variations on the arrangements of apparatus of FIGS. 5 through 8.

Addressing FIG. 9, permeate 71 from the first membrane stage membrane 64, passes through compressor 70, if present, and is fully or partially condensed in a reboiler heat exchanger 69. The fully or partially condensed permeate stream 84 passes through a back pressure controller 85 before returning to stripping column 60. Permeate vapor, 86, from the second stage membrane 67 is compressed in vacuum compressor 82 and is returned to the suction side of compressor 63. Retentate vapor (stream 68) is optionally condensed by heat exchange with the reboiler 69.

Figure 10:
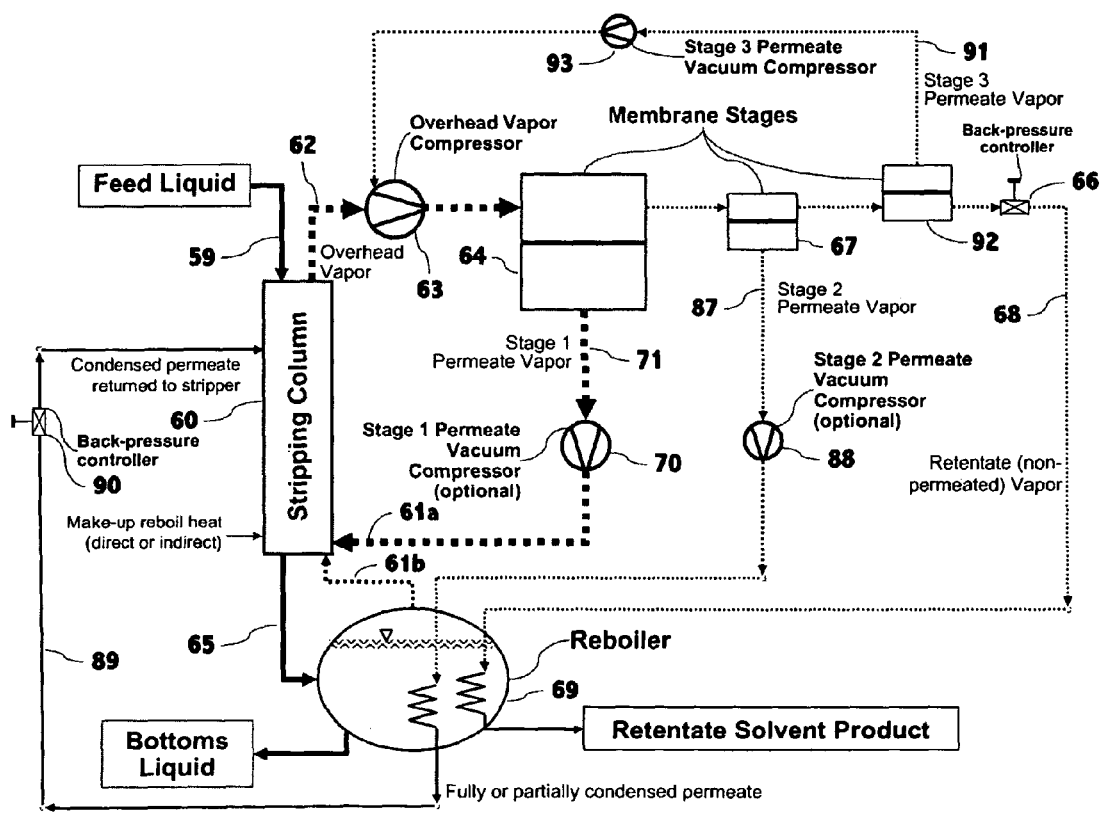

Referring to FIG. 10, consisting of three membrane stages in which permeate from the first membrane stage, 64 is returned as vapor through compressor 70 to act as stripping vapor stream 61a in the stripping column 60. Permeate (stream 87) from second stage membrane, 67, is directed to a heat exchanger in thermal contact with reboiler 69 to condense all or a portion of the permeate vapor from the second membrane stage. Permeate stream 87 may be compressed in a vacuum compressor, 88, before contacting the reboiler heat exchanger. After passing through the heat exchanger, the at least partially condensed stage 2 permeate stream, 89, is returned to the stripping column through a back-pressure regulator, 90. Permeate (stream 91) from the third stage membrane 92 is compressed with compressor 93 and returned to the suction side of the overhead compressor 63. Retentate vapor 68 is optionally condensed by heat exchange with the reboiler. The condensing permeate and product vapors causes liquid in the reboiler to vaporize, vapor created in this manner is returned to the stripping column as stream 61*b* and acts as a stripping agent.

In FIG. 11 shows a process according to the present invention consisting of three membrane stages in which permeate (stream 71) from the first membrane stage 64 is returned as vapor 61*a* to act as stripping vapor in the stripping column. Permeates from second stage membrane 67 and third stage membrane 94 are returned to the suction side of the overhead compressor 63. Third stage permeate (stream 95) is compressed in compressor 96 and then joins second stage permeate (stream 97) before returning to overhead compressor 63. The combined second and third stage permeate may be compressed in optional compressor 98. Retentate vapor 68 is optionally condensed by heat exchange with the reboiler 69, thereby generating vapor stream 61*b* which is returned to the stripping column 60.

Figure 12:
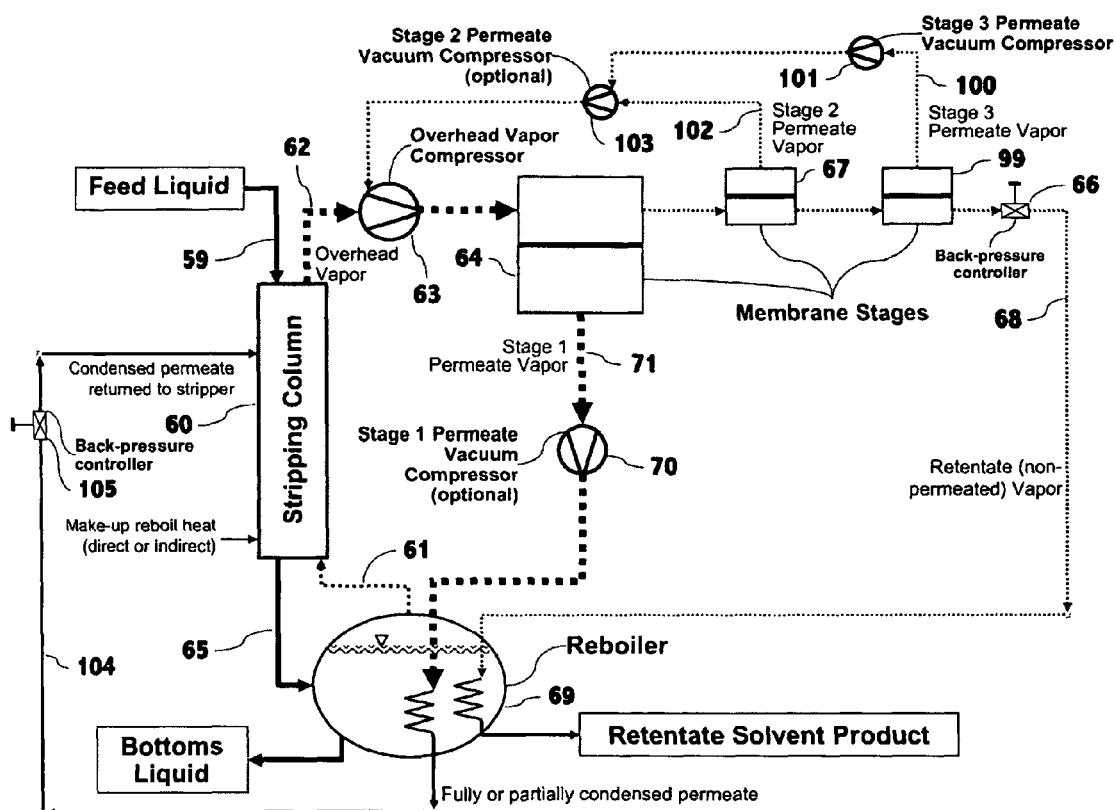

In FIG. 12 shows the process according to the present invention consisting of three membrane stages in which permeate from the first membrane stage (stream 71) is condensed in a reboiler heat exchanger, 69, which causes liquid in reboiler to evaporate and return to the stripping column 60 as vapor stream 61. As in FIG. 11, permeates from second stage membrane 67 and third stage membrane 99 are returned to the suction side of the overhead compressor 63. Third stage permeate (stream 100) is compressed in compressor 101 and then joins second stage permeate (stream 102) before returning to overhead compressor 63. The combined second and third stage permeate may be compressed in optional compressor 103. Retentate vapor is optionally condensed by heat exchange with the reboiler. The fully or partially condensed permeate from the first membrane stage (stream 104) passes through a back pressure controller 105 before returning to stripping column 60.

Figure 13:
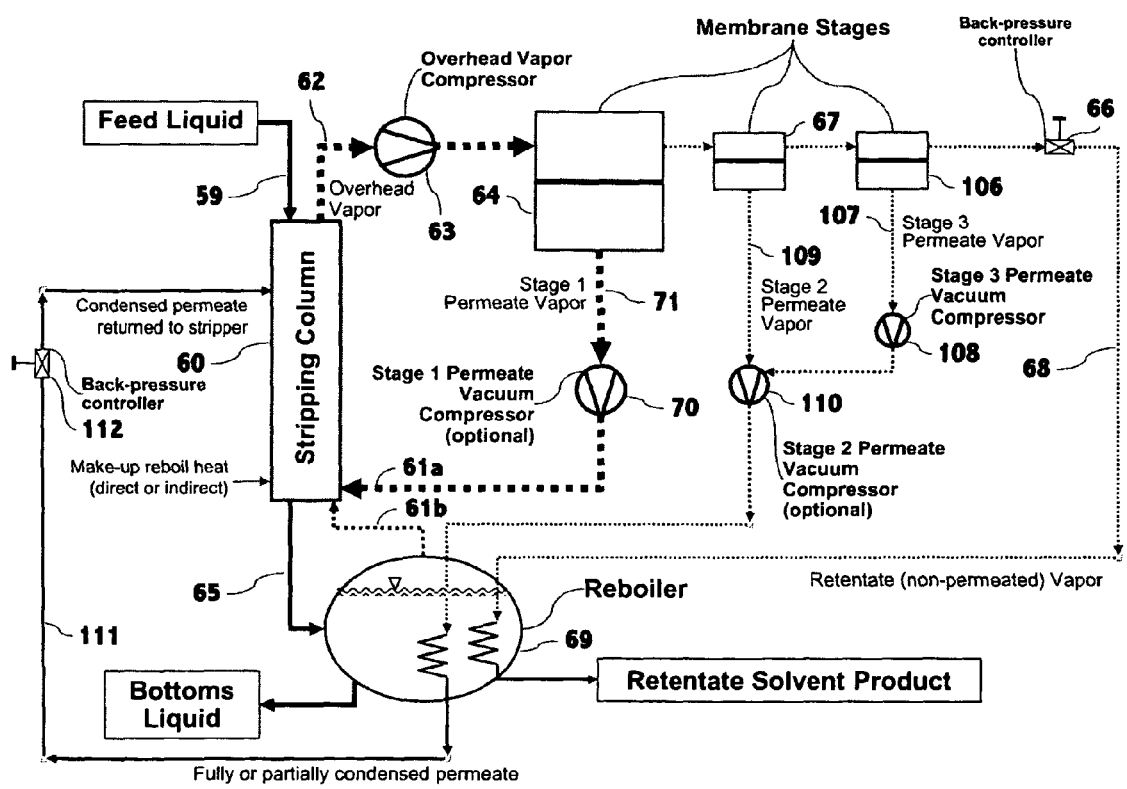

FIG. 13 shows a process according to the present invention consisting of three membrane stages in which permeate (stream 71) from the first membrane stage, 64, is returned as vapor to act as stripping vapor (stream 61*a*) in the stripping column, 60. Permeates from second stage membrane 67 and third stage membrane 106 are at least partially condensed in a reboiler heat exchanger, 69, to recover the heat of condensation. Third stage permeate (stream 107) is compressed in compressor 108 and then joins second stage permeate (stream 109) before entering reboiler heat exchanger. The combined second and third stage permeate may be compressed in optional compressor 110. Retentate vapor (stream 68) is optionally condensed by heat exchange with the reboiler. The fully or partially condensed permeate from the second and third membrane stages (stream 111) passes through a back pressure controller 112 before returning to stripping column 60.

Figure 14:
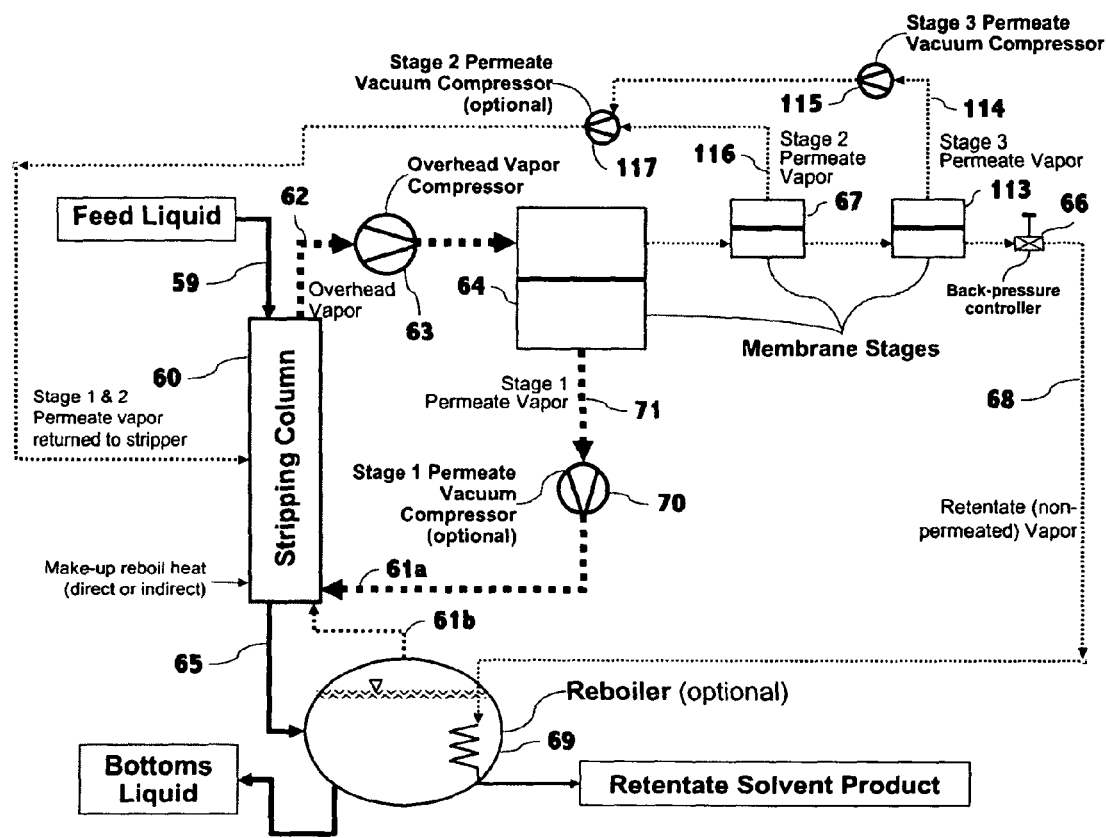

FIG. 14 is a schematic diagram of a process according to the present invention consisting of three membrane stages in which permeate (stream 71) from the first membrane stage, 64, is returned as vapor to act as stripping vapor in the stripping column, 60, as previously taught. Permeates from second stage membrane 67 and third stage membrane 113 are returned to an intermediate stage of the stripping column, 60. Third stage permeate (stream 114) is compressed in compressor 115 and then joins second stage permeate (stream 116) before returning to the stripping column 60. The combined second and third stage permeate may be compressed in optional compressor 117. Retentate vapor 68 is optionally condensed by heat exchange with the reboiler 69, thereby generating vapor stream 61*b* which is returned to the stripping column 60.

FIG. 22 is a schematic diagram of a process according to the present invention consisting of a single membrane stage in which there is the feed liquid stream, 152, which feeds into the stripping column, 153. A stream of bottoms liquid or treated liquid, 154, exits the bottom of the stripping column. Said bottoms liquid can be used as the source of liquid for an optional reboiler, 162. The desired solvent product is contained in the vapor stream, 155, which passes through a compressor, 156, and contacts selective membrane, 157. Vapor which has passed through the permselective membrane stage, 157, is returned to the bottom of the stripping column as a vapor stream, 161*a*. Stream, 161*a*, containing permeate vapor, may be compressed in a compressor, 160. A stream which is does not selectively pass through membrane 157 is retained (retentate or non-permeated vapor) and passes as stream 159. Stream 159 may have therein a back-pressure controller, 158, placed within the stream. The retentate containing the solvent product can then pass through a heat exchanger in thermal contact with the reboiler, 162, so that at least a portion of the product condenses. The condensing product causes liquid in the reboiler to vaporize, vapor created in this manner is returned to the stripping column as stream 161*b* and acts as a stripping agent. The final product is removed as stream 163.

Example 5

Production of Concentrated Acetone/Butanol/Ethanol Mixture from Dilute Fermentation Broth Just as has been described in Examples 2, 3, and 4 for a binary solvent-water mixture, multi-solvent mixtures can be removed from water and dehydrated with the subject invention. An example of this is the recovery of mixed solvents from acetone/n-butanol/ethanol (ABE) fermentation broths. Typical ABE fermentation broths contain at most about 2.0 wt % solvents in the mass ratio of 3:6:1 A:B:E, although the exact concentration and ratio is dependent on the organism and conditions of the fermentation. In a process of the present invention, the ABE broth would be fed to the top of a vapor stripping column. The overhead vapor would contain the ABE with very high solvent recovery. Due to high water-acetone and water-butanol permselectivities possible with dehydration membranes, it is likely that the permeate vapor from the first membrane stage, equipped with water-selective membranes, would be returned directly to the stripping column as vapor. Thus, one possible schematic diagram would be that of FIG. 5. The membrane retentate vapor would contain mixed ABE solvent with little water. The separation of these solvents from water by simple distillation is complicated for the following reasons:

n-butanol and ethanol each form azeotropes with water, mixtures of n-butanol and water phase separate into two liquid phases above about 7 wt % butanol, n-butanol boils at a higher temperature than water while ethanol and acetone boil at lower temperatures than water.

The present invention avoids those problems by processing the material in a vapor state in the concentration regions of concern.

Example 6

Recovery of Methanol from Methanol-Water Mixture

Using processes equivalent to those described in Examples 2, 3, and 4, methanol can be removed from water-based solutions. One potential use would be the recovery of methanol from condensate streams in Kraft pulping processes. The methanol could be recovered for use as a fuel or for reuse/use in another process.

Example 7

Separation of Ethanol/Toluene Mixture

The applications of the present invention described in examples 1-6 involve the separation of mixtures containing water as the major component of the liquid feed stream. The present invention can also be applied to the separation of mixtures of organic solvents with no water present. An example of this is the separation of ethanol/toluene mixtures. The separation of this mixture by distillation is complicated by the presence of an azeotrope at 32 wt % toluene. A feed stream containing less than 10 wt % ethanol is fed to a vapor stripping column according to the present invention. The overhead from the stripper is then enriched in ethanol relative to the feed stream. The compressed overhead vapor is then passed through toluene-selective membrane modules made of silicone rubber. The toluene-rich permeate vapor is sent back to the column as stripping vapor, according to the schematic diagram of FIG. 5. The product streams are an ethanol-enriched retentate vapor/condensate and a toluene-enriched bottoms stream from the stripping column.

Example 8

Drying of N-methyl-2-pyrrolidinone

The present invention described in examples 1-6 involve the separation of mixtures containing water as the major component of the liquid feed stream and where water is concentrated in the bottoms stream from the vapor stripping column. The present invention can also be used to remove trace amounts of water from mixtures of organic solvents and water in which the bottoms stream from the stripping column is enriched in the organic solvent and the overhead vapor is enriched in water. N-methyl-2-pyrrolidinone (NMP) is a common industrial solvent with a high boiling point (202° C.). NMP is also hygroscopic and will absorb water from the atmosphere. A water-NMP liquid mixture containing less than 10 wt % water is fed to the stripping column of the subject invention. The overhead vapor from the stripping column is then compressed and fed to NMP-selective membrane modules with the NMP-enriched permeate vapor returned to the stripping column or used to heat the reboiler via condensation. For example, polyurethaneurea membranes have been demonstrated to be selective for NMP. Schematic diagrams for such a process are shown in FIGS. 15-18. Alternatively, a water-selective membrane can be used to create an NMP-enriched retentate vapor. In either case, the bottoms liquid from the stripping column would be a dehydrated NMP stream.

Figure 15:
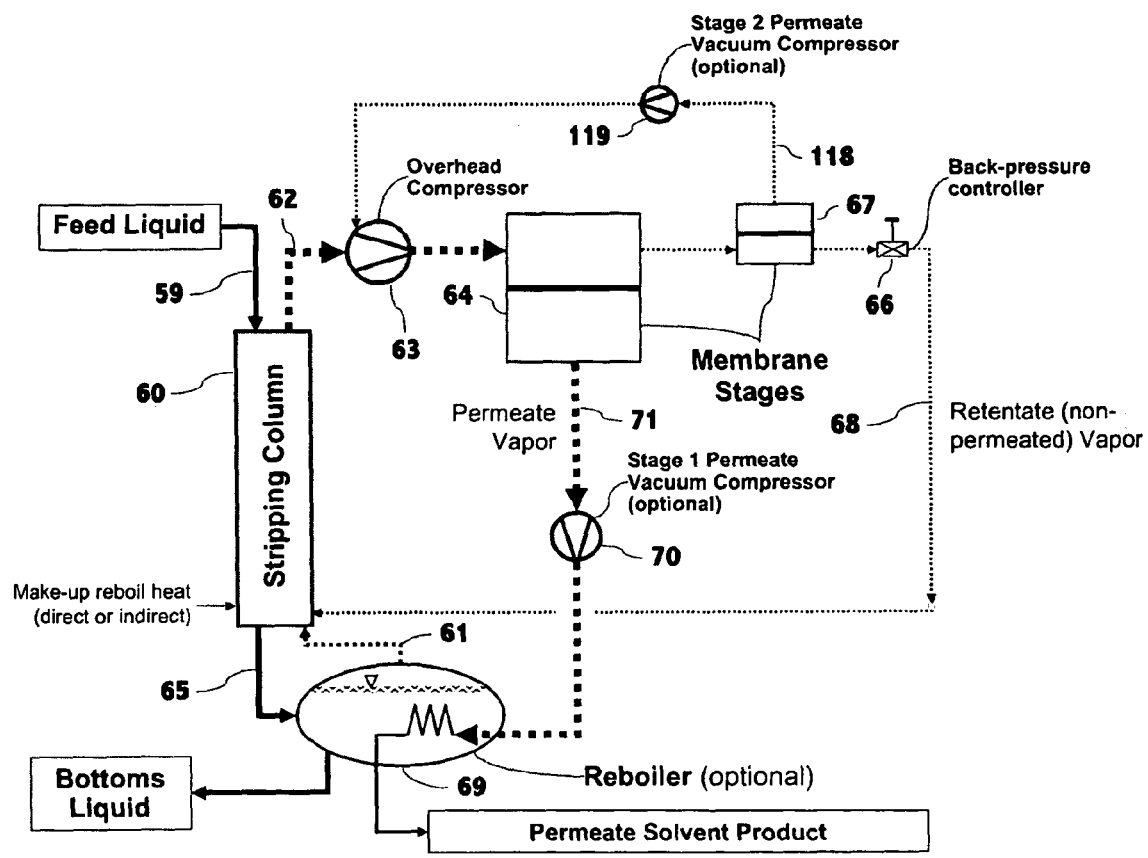

Referring with greater specificity to the figures, FIG. 15 is a schematic diagram of a process according to the present invention consisting of two membrane stages 64 and 67 in which the retentate stream, 68, from the membrane system is returned as vapor to act as stripping vapor in the stripping column 60. Permeate, (stream 71) from the first membrane stage is (optionally) condensed in a reboiler heat exchanger 69, generating stripping vapor stream 61. Stream 71 may be compressed in optional compressor 70 prior to condensation. Permeate (stream 118) from the second membrane stage, 67, is directed to the suction side of the overhead compressor, 63, and may be compressed in optional compressor 119 beforehand.

Figure 16:
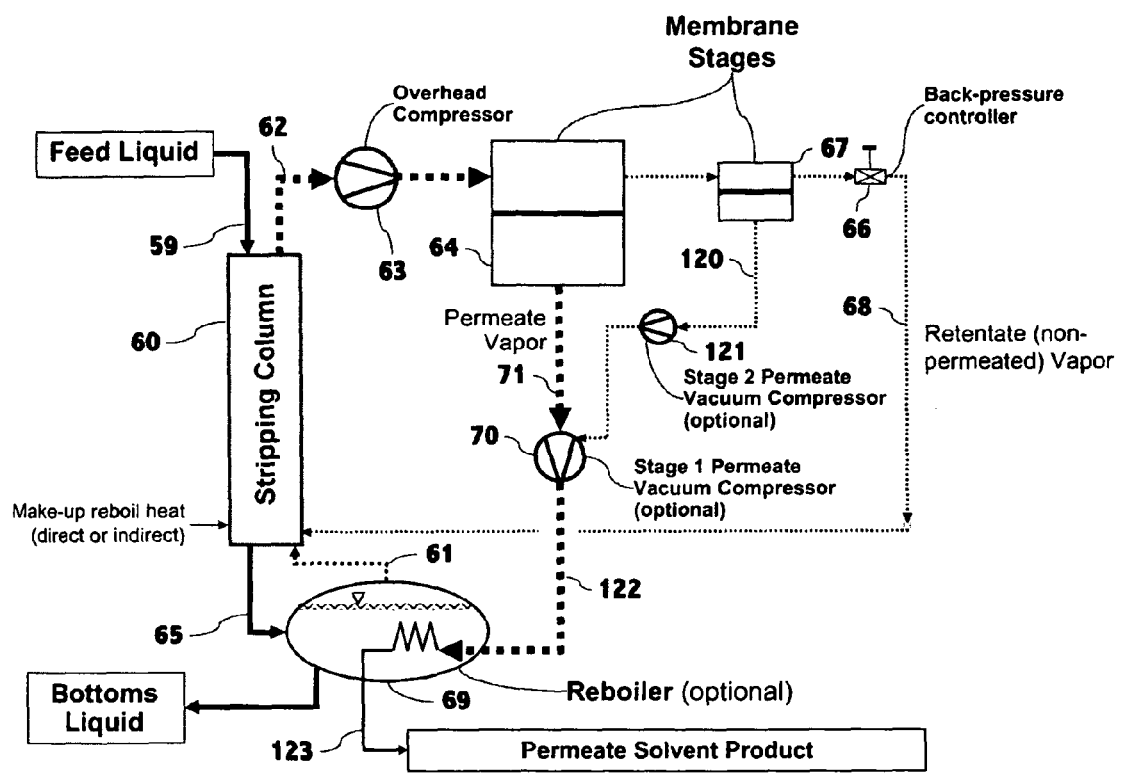
Figure 17:
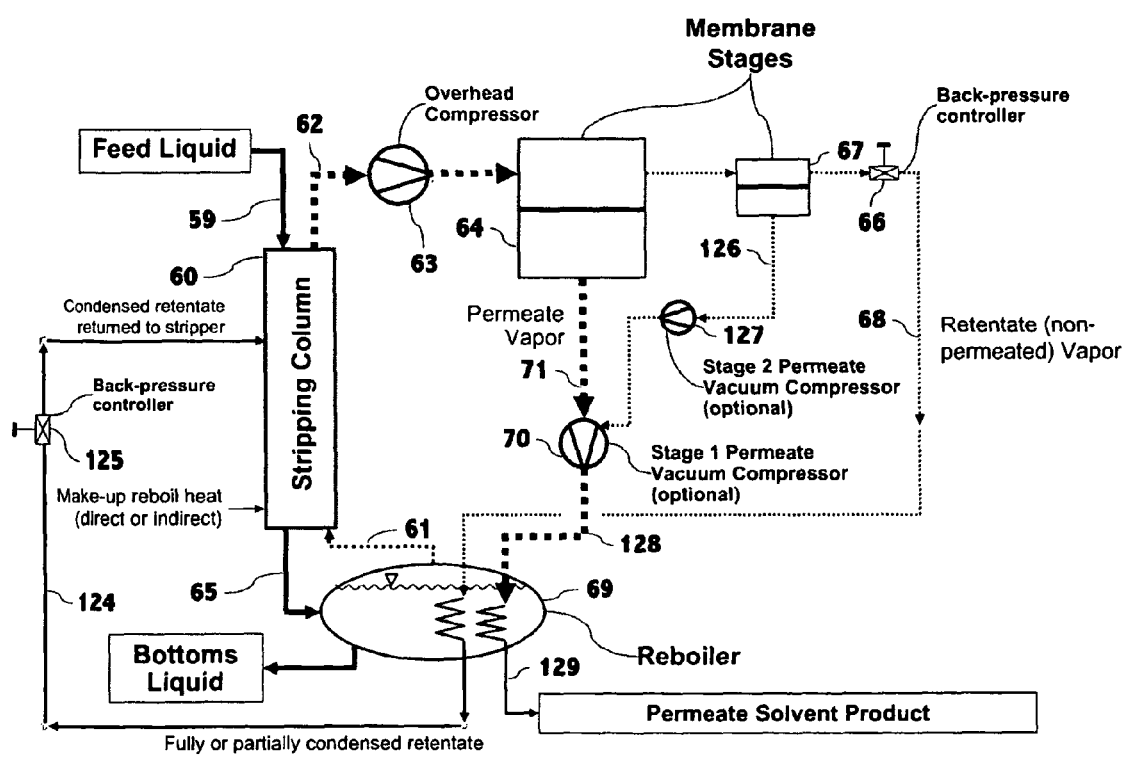

FIG. 16 is a schematic diagram of a process according to the present invention consisting of two membrane stages, 64 and 67, in which, as in the FIG. 15 example, retentate stream 68 from the membrane system is returned as vapor to act as stripping vapor in the stripping column 60. The permeate (stream 120) from the second membrane, 67, may be compressed in optional compressor 121 and joins the permeate vapor stream, 71, from the first membrane, 64. The combined permeate streams may be compressed in optional compressor, 70, if present. The combined permeate vapor streams, 122, are at least partially condensed in a heat exchanger in thermal contact with reboiler, 69, before exiting the system as at least partially condensed solvent product (stream 123). The condensing permeate vapors generate a vapor in the reboiler (stream 61) which is returned to the stripping column FIG. 17 is a schematic diagram of a process according to the present invention consisting of two membrane stages in which retentate (stream 68) from the membrane system is at least partially condensed in a reboiler heat exchanger, 69, and then returned to the stripping column (as stream 124) through a back-pressure controller, 125. Combined permeate from the membrane system is condensed in a reboiler heat exchanger. As in the FIG. 16 example, the permeate (stream 126) from the second membrane, 67, may be compressed in optional compressor 127 and joins the permeate vapor stream, 71, from the first membrane, 64. The combined permeate streams may be compressed in optional compressor, 70, if present. The combined permeate vapor streams, 128, are at least partially condensed in a heat exchanger in thermal contact with reboiler, 69, before exiting the system as at least partially condensed solvent product (stream 129). The condensing permeate and retentate vapors generate a vapor in the reboiler (stream 61) which is returned to the stripping column.

Figure 18:
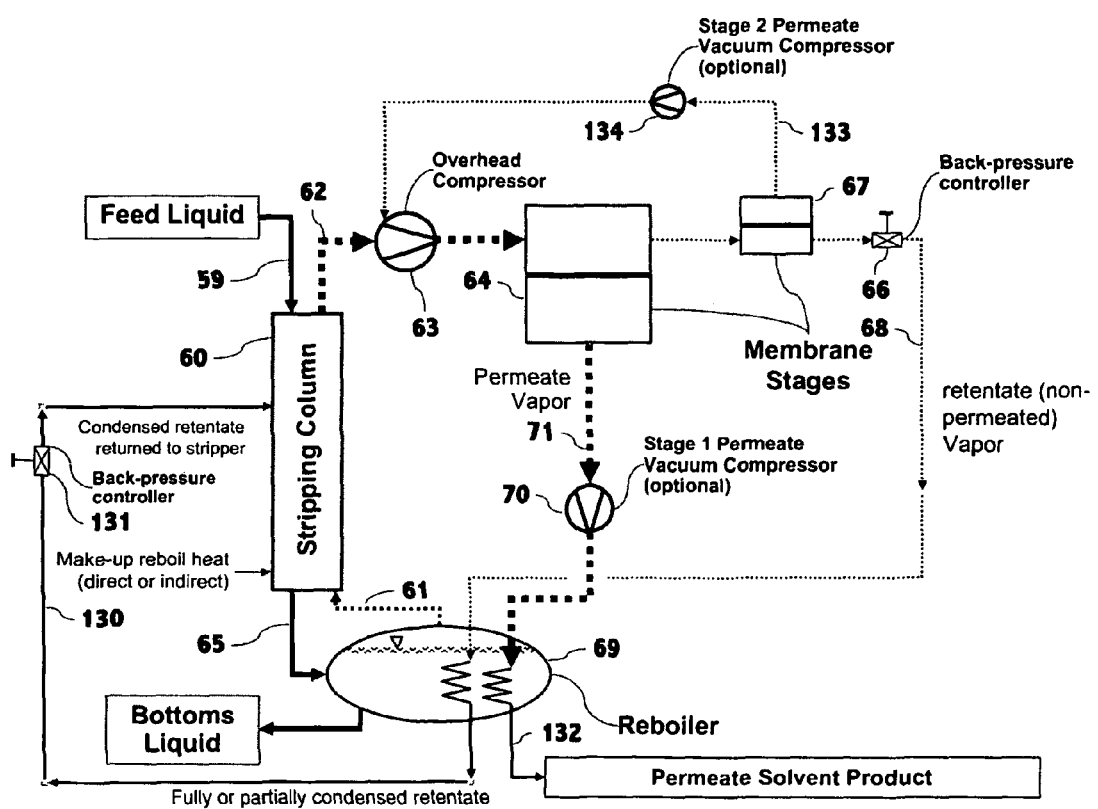

FIG. 18 is a schematic diagram of a process according to the present invention consisting of two membrane stages, 64 and 67, in which retentate (stream 68) from the membrane system is at least partially condensed in a reboiler heat exchanger, 69, and then returned to the stripping column (as stream 130) through a back-pressure controller, 131. Permeate vapor (stream 71), from stage 1 of the membrane system is at least partially condensed in a reboiler heat exchanger, 69, and exits the system as solvent product stream 132. Permeate vapor (stream 133) from stage 2 of the membrane system is returned to the suction side of the overhead compressor, 63. The pressure of permeate stream 133 may be increased with an optional compressor 134 before return to the overhead compressor. Vapor created in the reboiler by condensing permeate or retentate vapors is returned as stream 61 to the stripping column 60.

Example 9

Separation of Ethanol-Water Mixtures

An 8-stage vapor stripping column, diaphragm vacuum compressor, and vapor permeation module with silica perm-selective layer is used. The feed to the vapor stripping column is a 5 wt % ethanol solution. The vapor stripper is evaluated using pure steam as the added stripping gas to assess the amount of reboiler energy required for the separation. Then, the permeate vapor from the silica module is returned to the stripping column as the stripping vapor. Pure steam is added as an auxiliary heat source. The amount of steam required with and without permeate vapor return is then determined to evaluate energy consumption and savings.

Relating to the particular materials used in the examples, the stripper was a vertical stainless steel pipe (3" inner diameter) containing 3" diameter sections of Koch-Glitsch BX stainless steel wire gauze packing. Fourteen (14) 6.75" tall sections are inserted end-to-end in the column, yielding a total packing height of 7.88 feet. This packing material has a dry surface area of 1200 square feet/cubic foot. The stripper is thermally insulated from the ambient atmosphere with rubber foam. Feed liquid is metered into the top of the stripper with a peristaltic pump (Cole-Parmer Masterflex Pump) through a ¼" diameter stainless steel tube with liquid distribution slits. Vapor exits the top of the column through a stainless steel pipe connected in series with a Teflon-lined hose. Vapor enters the bottom of the stripping column through a stainless steel pipe. Liquid leaving the bottom of the stripping column is collected in a 1-gallon stainless steel vessel and periodically transferred to a receiving tank.

Compressor: A diaphragm vacuum pump (ILMVAC LP, Model MP 1201Ep) compresses the overhead vapor from the sub-atmospheric pressure of the stripping column and directs the compressed vapor to the membrane module inlet. The heads of the compressor are heat traced to prevent condensation of the process vapors (McMaster Can high temperature self regulating heat trace). A vacuum controller regulates the vacuum level applied to the stripper (LJ Engineering, Model 329L) Membrane module: A multi-tube ceramic membrane module with a silica permselective layer is used (Pervatech BV, Model PVM-500-10-7). The silica membranes are hydrophilic and preferentially permeate water relative to alcohols, such as ethanol. Seven (7) ceramic tubular membranes, each 50 cm long, are sealed with o-rings into a stainless steel module housing. Alternatively, a spiral wound membrane module fabricated with water-selective polymer membranes is used (Membrane Technology and Research, Inc.). Permeate from the membrane module is directed to the bottom of the stripping column through Teflon-lined hoses and stainless steel tubing or pipes. Retentate from the membrane module is condensed in a series of glass condensers (ACE Glass, Model 5956-145) which are cooled to 0 deg C. with a recirculation chiller (Neslab Coolflow CFT-150). A back pressure regulator controls the retentate pressure in the membrane module (GO Regulator, Model SBPR-1A51K5A113).

The steam source was auxiliary steam generated by metering deionized water into an evaporator using a peristaltic pump (Cole-Parmer Masterflex Pump). The steam is directed to the bottom of the stripping column using heat-traced stainless steel tubing and Teflon-lined hoses.

Example 10

Use of Fractional Condenser to Recover Heat from Permeate Vapors

This example involves the use of a fractional vapor condenser termed a "dephlegmator" to recover heat from permeate vapor stream(s). It is a modification of the scenario shown in FIG. 5. As in Example 2, a fermentation broth containing ethanol is fed (stream 135) into the top of a stripping column, 136. Ethanol-enriched overhead vapor from the stripping column (stream 137) is compressed in a vapor compressor, 138, and directed to two membrane stages in series, 139 and 140. The membranes are water-selective such that the permeate is enriched in water while the retentate stream is enriched in ethanol relative to the feed vapor to the membrane stage. In this example, permeate from membrane stage 1 (stream 141) and stage 2 (stream 142) are combined (stream 143) and directed, after being compressed (compressors 144 and 145), to the bottom of a fractional condenser called a dephlegmator, 146. The dephlegmator in this scenario is in the form of a high surface area heat exchanger. The permeate vapor rises on one side ("Vapor Side") of the heat exchange surface while a cooling liquid flows down the other side of the heat exchange surface ("Coolant Side"). Cooling for the dephlegmator is provided from liquid drawn from the bottom of the stripping column, possibly from an optional reboiler, 147. The cooling liquid is pumped (pump 148) into the coolant section of the dephlegmator at the top of the dephlegmator and withdrawn from the bottom. The coolant is warmed as it flows down through the dephlegmator, picking up heat from the rising vapor on the vapor side of the unit. The coolant liquid is returned to the bottom of the stripping column or to the reboiler through a pressure regulator, 149. The pressure in the coolant side of the dephlegmator is elevated relative to that in the stripping column to avoid boiling of the liquid as it is warmed in the dephlegmator. Upon return to the stripping column, a portion of the cooling liquid will evaporate due to the increase in temperature of the liquid after passing through the dephlegmator and the reduction in pressure upon return to the stripping column or reboiler.

Figure 21:
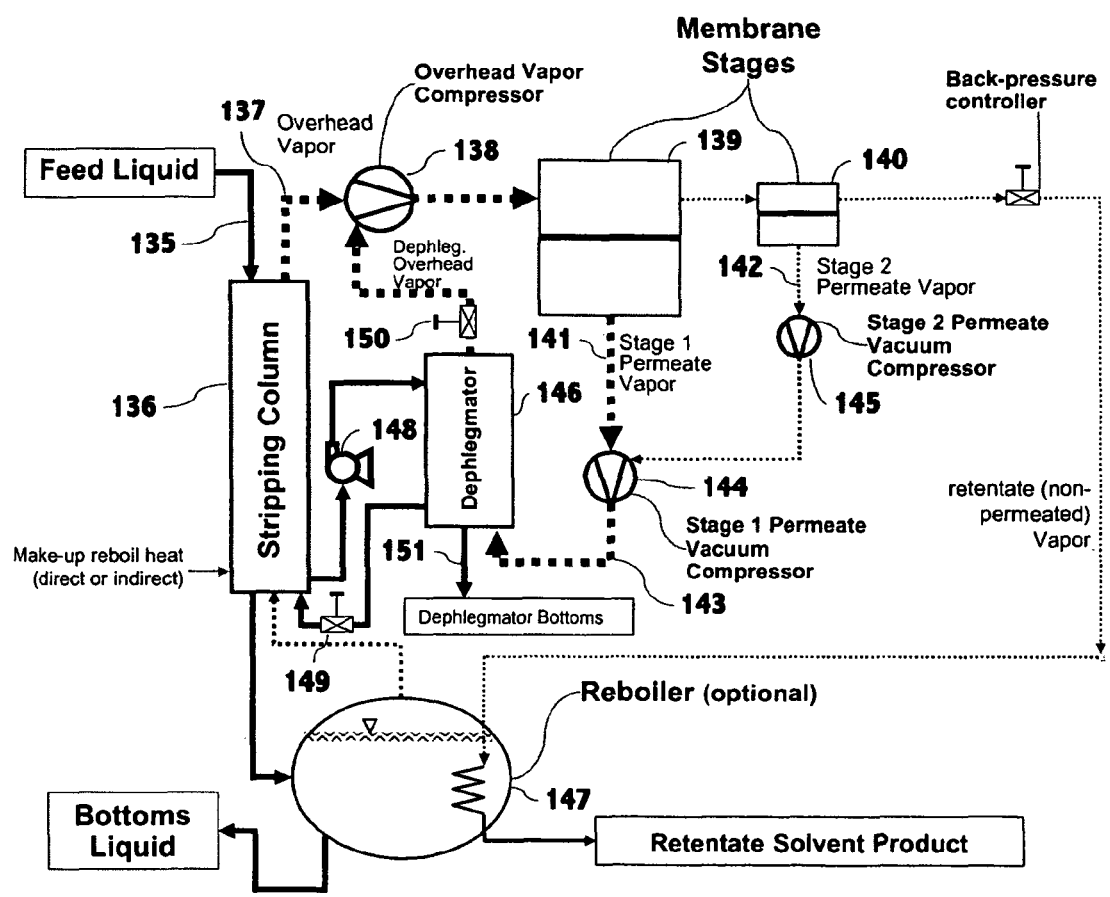
FIG. 21 shows the use of a fractional condenser to recover heat from permeate vapors and perform an additional separation of the vapor.

A portion of the rising vapor on the Vapor Side of the heat exchanger is condensed as it passes through the dephlegmator. Water preferentially condenses relative to ethanol, resulting in the rising vapor becoming enriched in ethanol. The vapor leaving the top of the dephlegmator is directed through a pressure regulator, 150, either to the stripping column or to the overhead compressor as shown in FIG. 21. The overhead vapor from the dephlegmator will be at a pressure higher than that of the stripping column and may be returned to an intermediate point in the compressor system or may utilize a secondary compressor before returning to the membrane system. The dephlegmator overhead vapor is enriched in ethanol relative to the permeate vapor. Condensate formed on the vapor side of the heat exchanger ("Dephlegmator Bottoms", stream 151) is removed from the bottom of the dephlegmator and is either returned to the stripper at the top of the stripper or at an intermediate point for additional ethanol recovery or, if sufficiently depleted in ethanol, is directed out of the treatment unit. For example, A heat exchange dephlegmator constructed to have ten vapor-liquid equilibrium stages is fed a permeate vapor containing 5 wt % ethanol (balance water) and is cooled with bottoms liquid from a stripper operating at a pressure of 198 torr such that the temperature at the bottom of the stripper is 66° C. Coolant flow rate is adjusted such that 80 wt % ethanol vapor is removed from the top of the dephlegmator at a pressure of 545 torr and is directed to the second stage of a multi-stage overhead compressor for reprocessing through the membrane stages. The bottoms liquid from the dephlegmator is returned to the stripping column at an intermediate stage at a temperature of 85° C. and containing 0.3 wt % ethanol. Alternatively, heat from the dephlegmator bottoms liquid can be transferred to liquid in the bottom or reboiler of the stripping column via a heat exchange device. The coolant is returned to the bottom of the stripping column through Reg. A at a temperature of 80° C. where it transfers heat to the bottoms liquid in the stripper.

The scenario depicted in FIG. 21 provides both recovery of heat from condensation of a portion of the permeate vapor as well as enriching of the permeate vapor so that ethanol in the permeate can be returned, as vapor, to the membrane stages. Fractional condensing dephlegmators may be used in similar manners to recover heat from individual permeate streams or from retentate streams and to achieve an additional separation of the vapor components in those streams.

In the general practice of the invention, the streams could flow through any appropriate tubing in moving from one component to another of the apparatus. In an industrial setting, metal tubing that is inert to the streams moving through the system would be appropriate. Obviously, the size and power of any component will be adjusted depending on the size of the operation and the composition flowing through the system.

For use in the stripping column, most packing materials used in such columns would be used. Examples include random packing such as balls, rings, saddles, or disks as well as structured materials such as plates, tubes, grids, mesh structures, and standard distillation trays such as disc-and-donut and bubble-cap trays.

It should be clear to one skilled in the art that the methods and the many variations on the apparatus of the invention can be used to separate a wide verity of solutions, including, for example, those wherein solvent "A" is water and the other solvents are organic compounds including methanol, ethanol, 1-propanol, 2-propanol, 1-butanol, tert-butanol, isobutanol, 2-butanol, acetone, butyl acetate, ethyl acetate, methyl ethyl ketone, tetrahydrofuran, methyl isobutyl ketone, dioxane, acetonitrile.

Additional solvent pairs include, but are not limited to:

Methanol+acetone (silicone rubber membrane, permeate enriched in acetone)

Methanol+acetone (polyvinyl alcohol membrane, permeate enriched in methanol)

Toluene+methanol (silicone rubber membrane, permeate enriched in toluene) Heptane+methanol, (silicone rubber membrane, permeate enriched in heptane)

Heptane+ethanol, (silicone rubber membrane, permeate enriched in heptane) Hexane+methanol, (silicone rubber membrane, permeate enriched in heptanes)

Hexane+ethanol, (silicone rubber, permeate enriched in heptane)

Hexane+2-propanol, (silicone rubber membrane, permeate enriched in heptane)

Ethyl acetate+ethanol, (silicone rubber membrane, permeate enriched in ethyl acetate)

Hexane+methyl isobutyl ketone, (silicone rubber membrane, permeate enriched in hexane).

Various permselective materials which could be used to make membranes useful in the present invention include, but are not limited to, poly(vinyl alcohol), NaA zeolite, Y-type Zeolite, ZSM-5 zeolites, Silicalite-1, Zeolite Beta, poly(allyl amine hydrochloride), chitosan, functionalized chitosan, sodium alginate, silicone rubber, polysiloxane, poly(dimethylsiloxane), poly(methylhydrosiloxane), poly(octylmethylsiloxane), poly(methyl phenyl siloxane), polysilicone, fluorinated silicone rubber, fluoropolymers, poly(methyl methacrylate), poly(trimethylsilylpropyne) "PTMSP", silica, surface-modified silica, polyurethane, poly(vinyl pyrollidone), zirconia, polyaniline, microporous alumino-phosphate, VITON™, EPDM, styrene-butadiene copolymers, poly(vinylidene fluoride), cellulose, ion exchange materials, nitrile-butadiene copolymers, polyelectrolytes, polyacrylic acid, polyimide, poly(ether-block-amide) [PEBA] copolymer, poly(ethylene oxide), poly(siloxaneimide), polyethylene, polypropylene, polyphosphazene, poly(ether ether ketone) [PEEK], sulfonated poly(ether ether ketone) [SPEEK], poly(4-methyl-2-pentyne) [PMP], polyglycols, poly(ethylene glycol), poly(propylene gycol), polyethyleneimine, polyvinylamine, NAFION™, BTDA-TDI/MDI (P84) co-polyimide, poly(ether imide), Interpreting Polymer Networks, amorphous copolymers of 2,2-bis-trifluoromethyl-4,5-difluoro-1,3-dioxole and tetrafluoroethylene (amorphous TEFLONS AF™), poly(propylene oxide), amorphous fluoropolymers, and mixtures, copolymers, blends, and mixed-matrix compositions thereof, including layered composite membranes.

What we claim is:

1. A process for separating a liquid feed mixture of two or more solvents in which one solvent ("A") predominates with other dilute solvent present at concentrations less than 50 mole %, said process comprising the steps of:
   a. introducing a flow of a liquid feed mixture stream at the top of a vapor stripping column wherein the stripping column additionally contains a rising vapor phase, said vapor stripping column also containing devices inside the column which establish mass transfer surfaces for the interaction of vapor phase and liquid feed mixture streams whereby there is produced a bottoms liquid stream depleted in the more dilute compound and an overhead vapor stream,
   b. increasing the pressure of said overhead vapor stream using a mechanical overhead vapor compression device to produce a compressed vapor stream;
   c. passing the compressed vapor stream to a vapor permeation membrane system, the membrane system comprising: at least one permselective membrane having a feed side and a permeate side wherein the feed side of the permselective membrane is in contact with the compressed vapor stream and the permeate side of the permselective membrane is in contact with a vapor at a pressure reduced relative to that of the feed side;
   d. withdrawing from the permeate side of the membrane system a permeate vapor stream enriched in solvent "A" relative to the compressed vapor stream which was passed on to the feed side of the membrane,
   e. withdrawing from the feed side a retentate, non-permeated, vapor depleted in solvent "A",
   f. introducing at least a portion of the permeate vapor stream withdrawn in step d into the stripping column at the base of the stripping column, wherein a portion of sensible heat in the bottoms liquid stream of step a is transferred to the liquid feed mixture using a heat exchanger.

2. The process of claim 1 wherein the stripping column contains devices inside the column which establish mass transfer surfaces including high surface area structures.

3. The process of claim 1 wherein, in step c, the membrane system comprising multiple individual membrane modules plumbed in parallel or series relative to a feed vapor flow from which the permeate vapor stream is withdrawn.

4. The process of claim 1 wherein the reduced permeate side pressure is achieved by passing at least a portion of the permeate vapor stream through one or more vacuum compressors.

5. The process of claim 4 wherein the permeate vapor stream is passed through the one or more vacuum compressors prior to introduction of the at least a portion of the permeate vapor stream into the stripping column.

6. The process of claim 4 wherein the permeate vapor stream is passed through the one or more vacuum compressors prior to introduction of the at least a portion of the permeate vapor stream into the suction side of the overhead mechanical vapor compressor device.

7. The process of claim 1 wherein the retentate vapor is introduced into at least one reboiler heat exchanger so that all or a portion of the latent or sensible heat can be transferred from the retentate vapor to at least one reboiler.

8. The process of claim 1 wherein auxiliary heat is provided at the base of the stripping column by at least one of
direct introduction of steam to the column and
heating via one or more reboiler heat exchangers.

9. The process of claim 1 wherein solvent A is water and dilute solvents are chosen from organic compounds R wherein R is chosen from a group consisting of methanol, ethanol, 1-propanol, 2-propanol, 1-butanol, tert-butanol, isobutanol, 2-butanol, acetone, butyl acetate, ethyl acetate, methyl ethyl ketone, tetrahydrofuran, methyl isobutyl ketone, dioxane, N-methyl-2-pyrrolidinone and acetonitrile.

10. The process of claim 1 wherein the membrane system consists of one membrane stage.

11. The process of claim 1 wherein the membrane system consists of multiple membrane stages.

12. The process of claim 4 wherein the at least a portion of the permeate vapor stream is passed through the one or more vacuum compressors and the permeate vapor stream is subjected to a fractional condensation step, comprising:
   a) introducing at least one compressor discharge stream into a fractional condenser wherein the condenser contains mass transfer surfaces to promote interaction of vapor phases and devices in heat exchanging contact with the fractional condenser,
   b) removing at least a portion of the latent and sensible heat from the at least one compressor discharge stream,
   c) withdrawing from the bottom of the fractional condenser a bottoms fractional condenser liquid stream depleted in a more volatile solvent relative to the at least one compressor discharge stream,
   d) withdrawing from the top of the fractional condenser an overhead fractional condenser vapor stream enriched in the more volatile solvent relative to the at least one compressor discharge stream.

13. The process of claim 1 wherein, in step d, the membrane system comprising multiple individual membrane modules relative to a feed vapor flow from which the permeate vapor stream is withdrawn.

14. The process of claim 1 wherein, after step d, the permeate vapor stream is passed through one or more vacuum compressors and returned to said stripping column.

15. A process for separating a liquid feed mixture of two or more solvents in which one solvent ("A") predominates with the other dilute solvent present at concentrations less than 50 mole %, the process comprising the steps of:
   a. introducing a flow of the liquid feed mixture at the top of a vapor stripping column wherein the column additionally contains a rising vapor phase, the vapor stripping column also containing devices inside the column which establish mass transfer surfaces for the interaction of vapor and liquid streams producing a bottoms liquid stream depleted in the more dilute solvent,
   b. increasing the pressure of an overhead vapor stream from the column using a mechanical overhead vapor compression device; then passing the compressed vapor stream to a vapor permeation membrane system comprising: a permselective membrane having a feed side and a permeate side; wherein the feed side of the membrane is in contact with said compressed vapor stream, and wherein the permeate side of said membrane is in contact with a vapor at a pressure reduced relative to that of said feed side;
   c. withdrawing a permeate vapor stream from the permeate side enriched in solvent "A" relative to the feed side of the membrane,
   d. withdrawing from the feed side a retentate, non-permeated, vapor depleted in solvent "A",
   e. passing a portion of the permeate vapor stream through one or more vacuum compressors, and
   f. introducing at least a portion of the permeate vapor into the stripping column at the base of the column.

16. The process of claim 15 wherein the at least a portion of the permeate vapor stream passed through the one or more vacuum compressors is subjected to a fractional condensation step, comprising:
   i. providing a fractional condenser containing mass transfer surfaces for the interaction of vapor and liquid phases passing therein;
   ii. providing devices in heat exchanging contact with the fractional condenser;
   iii. introducing at least one discharge stream into the fractional condenser;
   iv. removing at least a portion of the latent and sensible heat from a compressor discharge stream so as to cause the partial condensation of components of the compressor discharge stream;
   v. withdrawing from the bottom of the fractional condenser a bottoms fractional condenser liquid stream depleted in the more volatile solvent relative to the compressor discharge stream;
   vi. withdrawing from the top of the fractional condenser an overhead fractional condenser vapor stream enriched in the more volatile solvent relative to the compressor discharge stream.

17. A process for separating a liquid mixture of two or more solvents in which one solvent ("A") dominates with another solvent present at concentrations of less than 50 mole %, said process comprising:
   a) introducing a flow of the liquid mixture at the top of a vapor stripping column wherein the stripping column comprises
      i) a rising vapor phase which removes the more dilute solvent from a falling liquid phase;
      ii) a bottoms liquid stream depleted in the more dilute compounds;
      iii) an overhead vapor stream depleted in solvent "A" relative to a feed liquid;
      iv) devices inside the column which establish mass transfer surfaces for the introduction of vapor and liquid phases, said transfer surfaces being selected from the group consisting of trays, wiped liquid films, falling liquid films, and packing materials,
   and wherein said column is heated by at least one heat exchanger thermally connected to a reboiler located at the bottom of the column;
   b. increasing the pressure of the overhead vapor stream by at least 100% by means of a mechanical overhead vapor compressor device;
   c. passing the compressed vapor stream to at least one permeation membrane system wherein the membrane system comprises a permselective membrane selective for a dilute solvent wherein the permselective membrane has a feed side and a permeate side configured such that the feed side of the permselective membrane is in contact with the compressed vapor stream,
   d. withdrawing a permeate vapor stream from the permeate side depleted in solvent "A" relative to the feed side of the membrane, and
   e. withdrawing from the feed side a retentate, non-permeated, vapor enriched in solvent "A".

18. The process of claim 17 wherein, after withdrawing the retentate, non-permeated vapor enriched in solvent "A" in step e), at least a part of the retentate vapor is introduced to the stripping column at the base of the column.

* * * * *